(12) United States Patent
Boyes et al.

(10) Patent No.: US 10,406,111 B2
(45) Date of Patent: Sep. 10, 2019

(54) GOLD/LANTHANIDE NANOPARTICLE CONJUGATES AND USES THEREOF

(71) Applicant: COLORADO SCHOOL OF MINES, Golden, CO (US)

(72) Inventors: Stephen G. Boyes, Denver, CO (US); Misty D. Rowe, Golden, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 14/637,130

(22) Filed: Mar. 3, 2015

(65) Prior Publication Data

US 2015/0258034 A1 Sep. 17, 2015

Related U.S. Application Data

(62) Division of application No. 13/202,311, filed as application No. PCT/US2010/024450 on Feb. 17, 2010, now Pat. No. 8,968,705.

(60) Provisional application No. 61/153,553, filed on Feb. 18, 2009.

(51) Int. Cl.
| | | |
|---|---|---|
| A61K 9/51 | (2006.01) | |
| A61K 49/00 | (2006.01) | |
| A61K 49/04 | (2006.01) | |
| A61K 49/12 | (2006.01) | |
| A61K 49/18 | (2006.01) | |
| B82Y 5/00 | (2011.01) | |
| A61K 33/24 | (2019.01) | |

(52) U.S. Cl.
CPC .......... *A61K 9/5115* (2013.01); *A61K 9/5138* (2013.01); *A61K 33/24* (2013.01); *A61K 49/0002* (2013.01); *A61K 49/0428* (2013.01); *A61K 49/126* (2013.01); *A61K 49/1824* (2013.01); *A61K 49/1878* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 4,708,930 A | 11/1987 | Kortright et al. | |
| 4,743,543 A | 5/1988 | Kortright | |
| 4,892,935 A | 1/1990 | Yoshida et al. | |
| 4,914,021 A | 4/1990 | Toth et al. | |
| 4,918,164 A | 4/1990 | Hellstrom et al. | |
| 4,921,789 A | 5/1990 | Salem et al. | |
| 4,921,790 A | 5/1990 | O'Brien | |
| 4,939,240 A | 7/1990 | Chu et al. | |
| 4,963,484 A | 10/1990 | Kufe | |
| 5,053,489 A | 10/1991 | Kufe | |
| 5,110,911 A | 5/1992 | Samuel et al. | |
| 5,270,163 A | 12/1993 | Gold et al. | |
| 5,475,096 A | 12/1995 | Gold et al. | |
| 5,512,443 A | 4/1996 | Schlom et al. | |
| 5,545,530 A | 8/1996 | Satomura et al. | |
| 5,693,763 A | 12/1997 | Codington et al. | |
| 5,808,005 A | 9/1998 | Codington et al. | |
| 5,855,866 A | 1/1999 | Thorpe et al. | |
| 5,892,019 A | 4/1999 | Schlom et al. | |
| 5,892,020 A | 4/1999 | Mezes et al. | |
| 6,270,748 B1 | 8/2001 | Annan et al. | |
| 7,102,024 B1 | 9/2006 | Schwartz et al. | |
| 7,402,690 B2 | 7/2008 | McCormick et al. | |
| 8,916,135 B2 | 12/2014 | Boyes | |
| 8,968,705 B2 | 3/2015 | Boyes et al. | |
| 9,175,015 B2 | 11/2015 | Boyes et al. | |
| 2002/0165179 A1 | 11/2002 | Baker, Jr. | |
| 2003/0199653 A1 | 10/2003 | McCormick, III et al. | |
| 2004/0052729 A1 | 3/2004 | Penades et al. | |
| 2005/0031692 A1 | 2/2005 | Beyerinck et al. | |
| 2006/0233712 A1 | 10/2006 | Penades et al. | |
| 2007/0123670 A1 | 5/2007 | McCormick et al. | |
| 2009/0031856 A1* | 2/2009 | Lee | B22F 9/24 75/343 |
| 2009/0060839 A1 | 3/2009 | Boyes et al. | |
| 2009/0060840 A1 | 3/2009 | Boyes et al. | |
| 2012/0052006 A1 | 3/2012 | Boyes et al. | |
| 2013/0116554 A1 | 5/2013 | Kaiser et al. | |

FOREIGN PATENT DOCUMENTS

| | | |
|---|---|---|
| WO | 93/11161 A1 | 6/1993 |
| WO | 9311161 | 6/1993 |
| WO | 94/13804 A1 | 6/1994 |
| WO | 1994013804 | 6/1994 |
| WO | 97/38134 A1 | 10/1997 |
| WO | 98/33941 A1 | 8/1998 |

(Continued)

OTHER PUBLICATIONS

Adlish, et al., "Identification of a Putative Cell Receptor for Human Cytomegalovirus", Virology (1990), 176, 337-345.

Ahrens, et al., "A model for MRI contrast enhancement using T1 agents", Proc. Nat'l. Acad. Sci. U.S.A. (1998), 95, 8443-8448.

Aime, et al., "A R2R1 Ratiometric Procedure for a Concentration-Independent pH-Responsive, GD(III)-Based MRI Agent", J. Am. Chem. Soc. (2006), 128, 11326-11327.

Allen, "Ligand-Targeted Therapeutics in Anticancer Therapy", Nat. Rev. Cancer (2002), 2, 750-763 and 2 pages.

Alric, Christophe, et al., "Gadoliniuim Chelate Coated Gold Nanoparticles as Contrast Agents for Both X-ray Computed Tomography and Magnetic Resonance Imating", J. Am. Chem. Soc., 130, 2008, 5908-5915.

Bakalova, et al., "Multimodal Silica-Shelled Quantum Dots: Direct Intracellular Delivery, Photosensitization, Toxic, and Microcirculation Effects", Bioconjugate Chem. (2008), 19, 1135-1142.

(Continued)

*Primary Examiner* — Tigabu Kassa
(74) *Attorney, Agent, or Firm* — Dorsey & Whitney LLP

(57) ABSTRACT

The present disclosure is directed generally to gold/lanthanide nanoparticle conjugates, such as gold/gadolinium nanoparticle conjugates, nanoparticle conjugates including polymers, nanoparticle conjugates conjugated to targeting agents and therapeutic agents, and their use in targeting, treating, and/or imaging disease states in a patient.

20 Claims, 9 Drawing Sheets

(56) References Cited

FOREIGN PATENT DOCUMENTS

WO    99/07724 A1    2/1999

OTHER PUBLICATIONS

Binkley, et al., "RNA ligands to human nerve growth factor", Nuc. Acids Res. (1995), 23(16), 3198-3205.

Bird, et al., "Single-Chain Antigen-Binding Proteins", Science (1988), 242, 423-426.

Bridot, et al., "Hybrid Gadolinium Oxide Nanoparticles: Multimodal Contrast Agents for in Vivo Imaging", J. Am. Chem. Soc. (2007), 129, 5076-5084.

Burda, et al., "Chemistry and Properties of Nanocrystals of Different Shapes", Chem. Rev. (2005), 105, 1025-1102.

Caravan, et al., "Gadolinium(III) Chelates as MRI Contrast Agents: Structure, Dynammics and Application", Chem. Rev. (1999), 99, 2293-2352.

Carel, et al., "Structural Requirements for C3d,g/Epstein-Barr Virus Receptor (CR2/CD21) Ligand Binding, Internalization, and Viral Infection", J. Biol. Chem. (1990), 265(21), 12293-12299.

Carter, "Potent antibody therapeutics by design", Nature Reviews Immunology (2006), 6, 343-357.

Chang, In Pin, et al., "Preparation of Fluorescent Magnetic Nanodiamonds and Cellular Imaging", J. Am. Chem. Soc., 2008, 130 (46), 1022/2008, 15476-15481.

Cheon, et al., "Synergistically Integrated Nanoparticles as Multimodal Probes for Nanobiotechnology", Accounts of Chem. Res., published online at www.pubs.acs.org/acr (Aug. 13, 2008), 1630-1640.

Co, et al., "Isolation and biochemical characterization of the mammalian reovirus type 3 cell-surface receptor", Proc. Nat'l. Acad. Sci. U.S.A (1985), 82, 1494-1498.

Dalgleish, et al., "The CD4 (T4) antigen is an essential component of the receptor for the AIDS retrovirus", Nature (1984), 312, 763-766.

Daniel, et al., "Gold Nanoparticles: Assembly, Supramolecular Chemistry, Quantum-Size-Related Properties, and Applications toward Biology, Catalysis, and Nanotechnology", Chem. Rev. (2004), 104(1), 293-346.

Eppstein, et al., "Epidermal growth factor receptor occupancy inhibits vaccinia virus infection", Nature (1985), 318, 663-665.

Ferrari, "Cancer Nanotechnology: Opportunities and Challenges", Nature Rev. Cancer (2005), 5, 161-171.

Frullano, et al., "Multimodal MRI Contrast Agents", J. Biol. Inorg. Chem. (2007), 12, 939-949.

Fu, et al., "Cascade Polymeric MRI Contrast Media Derived from Poly(ethylene glycol) Cores: Initial Syntheses and Characterizations", Biomacromolecules (2007), 8, 1519-1529.

Fustin, et al., "Tuning the hydrophilicity of gold nanoparticles templated in star block copolymers", Langmuir (2006), 22,, 6690-6695.

Hanisch, et al., "Structural Studies on Oncofetal Carbohydrate Antigens (CA 19-9, CA 50, and CA 125) Carried by O-Linked Sialyloligosaccharides on Human Amniotic Mucins", Carbohydr. Res. (1988), 178, 29-47.

Harlow, et al., "Using Antibodies: A Laboratory Manual", Cold Spring Harbor, New York, Cold Spring Harbor Laboratory Press, 1999, 5 pages.

Hifumi, et al., "Gadolinium-Based Hybrid Nanoparticles as a Positive MR Contrast Agent", J. Am. Chem. Soc. (2006), 128(47), 15090-15091.

High, et al., "Gadolinium is detectable within the tissue of patients with nephrogenic systemic fibrosis", J. Am. Acad. Dermatol. (2007), 56, 21-26.

Hinoda, et al., "Immunochemical Characterization of Adenocarcinoma-Associated Antigen YH206", Int'l Cancer Journal (1988), 42, 653-658.

Holliger, et al., "Diabodies: Small bivalent and bispecific antibody fragments", Proc. Natl. Acad. Sci. USA (1993) 90, 6444-6448.

Holliger, et al., "Engineered antibody fragments and the rise of single domains: Antibody engineering and manufacture", Nature Biotech (2005), 23(9), 1126-1136.

Huang, et al., "Cancer Cell Imaging and Photothermal Therapy in the Near-Infrared Region by Using Gold Nanorods", J. Am. Chem. Soc. (2006), 128, 2115-2120.

Huston, et al., "Protein engineering of antibody binding sites: Recovery of specific activity in an anti-digoxin single-chain Fv analogue produced in *Escherichia coli*", Proc. Natl. Acad. Sci. U.S.A. (1988), 85, 5879-5883.

Ishida, et al., "Related Glycoprotiens from Normal Secretory and Malignant Brest Cells: Purification and Intitial Comparative Characterizations", Tumor Biol. (1989), 10, 12-22 and 1 page.

Jellinek, et al., "Inhibition of Receptor Binding by High-Affinity RNA Ligands to Vascular Endothelial Growth Factor", Biochem. (1994), 33(34), 10450-10456.

Kaner, et al., "Fibroblast Growth Factor Receptor is a Portal of Cellular Entry for Herpes Simplex Virus Type 1", Science (1990), 248, 1410-1413.

Kim, et al., "Antibiofouling Polymer-Coated Gold Nanoparticles as a Contrast Agent for in Vivo X-ray Computed Tomography Imaging", J. Am. Chem. Soc. (2007), 129, 7661-7665.

Kjeldsen, "Preparation and Characterization of Monoclonal Antibodies Directed to the Tumor-associated O-linked Sailosyl-2-6 a-N-Acetylgalactosaminyl (Sialosyl-Tn) Epitope", Cancer Research (1988), 48, 2214-2220.

Klatzmann, et al., "T-lymphocyte T4 molecule behaves as the receptor for human retrovirus LAV", Nature (1984), 312, 767-768.

Konopacki, et al., "Polymer Modified Gold and Gadolinium Nanoparticles for Targeted Imaging and Treatment of Cancer", Department of Chemistry and Geochemstry Colorado School of Mines, Golden, Colorado, 2 pages, Polymer Preprints, 2007, 48(2).

Krah, et al., "Characterization of Octyl Glucoside-Solubilized Cell Membrane Receptors for Binding Measles Virus", Virology (1989), 172, 386-390.

Kukowska-Latallo, et al., "Nanoparticle Targeting of Anticancer Drug Improves Therapeutic Response in Animal Model of Human Epithelial Cancer", Cancer Research (2005), 65, 5317-5324.

Lan, et al., "Isolation and Properties of a Human Pancreatic Adenocarcinoma-associated Antigen, DU-PAN-2", Cancer Res. (1985), 45, 305-310.

Lentz, et al., "Is the Acetylcholine Receptor a Rabies Virus Receptor?", Science (1982), 215, 182-184.

Lowe, et al., "Facile preparation of transition metal nanoparticles stabilized by well-defined (Co)polymers synthesized via aqueous reversible addition-fragmentation chain transfer polymerization", J. Am. Chem. Soc. (2002), 124, 11562-11563.

Lu, et al., "Mesoporous Silica Nanoparticles as a Delivery System for Hydrophobic Anticancer Drugs", Small (2007), 3(8), 1341-1346.

Marlin, et al., "A soluble form of intercellular adhesion molecule-1 inhibits rhinovirus infection", Nature (1990), 344, 70-72.

Martin, et al., "Nanomaterials in Analytical Chemistry", Analytical Chem. News & Features, May 1, 1998, 322-327, 12 pages.

Mendelsohn, "Cellular Receptor for Poliovirus: Molecular Cloning, Nucleotide Sequence, and Expression of a New Member of the Immunoglobulin Superfamily", Cell (1989), 56, 855-865.

Murphy, et al., "Anisotropic Metal Nanoparticles: Synthesis, Assembly, and Optical Applications", J. Phys. Chem. B (2005), 109, 13857-13870.

Nasongkla, et al., "Multifunctional Polymeric Micelles as Cancer-Targeted, MRI-Ultrasensitive Drug Delivery Systems", Nano Letters (2006), 6(11), 2427-2430.

Niidome, et al., "PEG-modified gold nanorods with a stealth character for in vivo applications", J. Controlled Release (2006), 114, 343-347.

Odian, "Principles of Polymerization", 4th Edition, Hoboken, New Jersey, Wiley-Interscience, 2004, 19 pages.

Oyewumi, "Comparison of cell uptake, biodistribution and tumor retention of folate-coated and PEG-coated gadolinium nanoparticles in tumor-bearing mice", Journal of Controlled Release (2004), 95, 613-626.

(56) References Cited

OTHER PUBLICATIONS

Park, "Nanotechnology: What it can do for drug delivery", J. Controlled Release (2007), 120, 1-3.
Park, "Tumor-directed Targeting of Liposomes", Biosci. Rep. (2002), 22(2), 267-281.
Perez-Juste, et al., "Gold-nanorods: Synthesis, characterization and applications", Coordination Chemistry Reviews (2005), 249, 1870-1901.
Remington, "Remington: Practice of the Science and Pharmacy", 19th Edition, Alfonso R. Gennaro, ed., (1995) Chapter 83, 1447-1675 and 3 cover pages.
Rieter, et al., "Nanoscale Metal-Organic Frameworks as Potential Multimodal Contrast Enhancing Agents", J. Am Chem. Soc. (2006), 128, 9024-9025.
Rieter, et al., "Surface Modification and Functionalization of Nanoscale Metal-Organic Frameworks for Controlled Release and Luminescence Sensing", J. Am. Chem. Soc., May 17, 2007, 2 pages.
Rowe, et al., "Synthesis of Surface-Initiated Stimuli-Responsive Diblock Copolymer Brushes Utilizing a Combination of ATRP and RAFT Polymerization Techniques", Macromolecules (2008), 41(12), 4147-4157.
Rowe-Konopacki, et al., "Synthesis of Surface Initiated Diblock Copolymer Brushes from Flat Silicon Substrates Utilizing the RAFT Polymerization Technique", Macromolecules (2007), 40(4), 879-888.
Ruff, et al., "CD4 receptor binding peptides that block HIV infectivity cause human monocyte chemotaxis", FEBS Letters (1987), 211(1), 17-22.
Sacerdote, et al., "Vasoactive Intestinal Peptide 1-12: A Ligand for the CD4 (T4)/Human Immunodeficiency Virus Receptor", J. Neuroscience Research (1987), 18, 102-107 and 1 page.
Sau, et al., "Seeded High Yield Synthesis of Short Au Nanorods in Aqueous Solution", Langmuir (2004), 20(15), 6414-6420.
Sebra, "Surface Grafted Antibodies: Controlled Architecture Permits Enhanced Antigen Detection", Langmuir (2005), 21(24), 10907-10911.
Seevinck, et al., "Factors Affecting the Sensitivity and Detection Limits of MRI, CT, and SPECT for Multimodal Diagnostic and Therapeutic Agents", Anti-Cancer Agent in Medicinal Chemistry (Formerly Current Medicinal Chemistry—Anti-Cancer Agents), vol. 7, No. 3, May 2007, pp. 317-334(18).
Service, "Nanotechnology Takes Aim at Cancer", Science (2005), 310, 1132-1134.
Shepley, et al., "Monoclonal antibody identification of a 100-kDa membrane protein in HeLa cells and human spinal cord involved in poliovirus attachment", Proc. Nat'l. Acad. Sci. U.S.A. (1988), 85, 7743-7747.
Slavin, Stacy et al., "Adsorption behaviour of sulfur containing polymers to gold surfaces using QCM-D", Soft Matter, 2012, 8, 118-128, DOI: 10.1039/c1sm06410j.
Slowing, et al., "Mesoporous Silica Nanoparticles for Intracellular Delivery of Membrane-Impermeable Proteins", J. Am. Chem. Soc. (2007), 129, 8845-8849.
Solberg, et al., "Adsorption of DNA into Mesoporous Silica", J. Phys. Chem. B. (2006), 110(31), 15261-15268.
Springer, et al., "Blood Group Tn-Active Macromolecules from Human Carcinomas and Erythrocytes: Characterization of and Specific Reactivity with Mono- and Poly-Clonal Anti-Tn Antibodies Induced by Various Immunogens", Carbohydr. Res. (1988), 178, 271-292.
Stenzel, Martina H., "Hairy Core-Shell Nanoparticles via RAFT: Where are the Opportunities and Where are the Problems and Challenges?", Macromol. Rapid Commun. 2009, 30, 1603-1624, DOI: 10.1002/marc.200900180.
Su, et al., "Nanoshell Magnetic Resonance Imaging Contrast Agents", J. Am. Chem. Soc. (2007), 129, 2139-2146.
Sumerlin, et al., "Modification of gold surfaces with water-soluble (Co)polymers prepared via aqueous reversible addition—fragmentation chain transfer (RAFT) polymerization", Langmuir (2003), 19, 5559-5562.

Tjandra, et al., "Application of mammary serum antigen assay in the management of breast cancer: a preliminary report", Br. J. Surg. (1988), 75(8), 811-817.
Tomlinson, et al., "Methods for Generating Multivalent and Bispecific Antibody Fragments", Methods in Enzymology (2000), 326, 461-479.
Tuerk, et al., "In vitro evolution of functional nucleic acids: high-affinity RNA ligands of HIV-1 proteins", Gene. (1993), 137, 33-39.
Ward, et al., "Binding activities of a repertoire of single immunoglobulin variable domains secreted from *Escherichia coli*", Nature (Oct. 12, 1989), 341, 544-546.
Weis, et al., "Structure of the influenza virus haemagglutinin complexed with its receptor, sialic acid", Nature (1988), 333, 426-431.
White, et al., "Viral Receptors of the Immunoglobulin Superfamily", Cell (1989), 56, 725-728.
Wyrick, et al., "Entry of Genital Chlamydia trachomatis into Polarized Human Epithelial Cells", Infect. and Immunity (1989), 57(8), 2378-2389.
Yanjarappa, "Synthesis of Copolymers Containing an Active Ester of Methacrylic Acid by RAFT: Controlled Molecular Weight Scaffolds for Biofunctionalization", Biomacromolecules (2006), 7(5), 1665-1670.
Zola (Ed.), "Monoclonal Antibodies: Preparation and use of monoclonal antibodies and engineered antibody derivatives," 2000, Springer Verlag, 1st Edition, 1st Edition, New York, New York, Springer Verlag, 2000, 5 pages.
International Bureau, "PCT International Search Report dated Dec. 19, 2008", PCT Application No. PCT/US2008/74065, filed Aug. 22, 2008, 3 pages.
International Bureau, "International Search Report and Written Opinion", PCT/US2010/024450, dated Jul. 24, 2010; 8 pages.
U.S. Patent and Trademark Office, "U.S. Restriction/Election Requirement dated Feb. 4, 2011", U.S. Appl. No. 12/197,044 8 pages.
U.S. Patent and Trademark Office, "U.S. Response to Election/Restriction dated Mar. 4, 2011", U.S. Appl. No. 12/197,044, 7 pages.
U.S. Patent and Trademark Office, "U.S. Notice of Non-Final Rejection dated May 19, 2011", U.S. Appl. No. 12/197,044 7 pages.
U.S. Patent and Trademark Office, "U.S. Requirement for Restriction/Election dated Jun. 3, 2011", U.S. Appl. No. 12/197,061, 6 pages.
U.S. Patent and Trademark Office, "U.S. Response to Election/Restriction dated Jul. 5, 2011", U.S. Appl. No. 12/197,061, 6 pages.
U.S. Patent and Trademark Office, "U.S. Non-Final Rejection Office action dated Oct. 7, 2011", U.S. Appl. No. 12/197,061, 12 pages.
U.S. Patent and Trademark Office, "U.S. Amendment and Response to Non-Final Office Action dated Nov. 21, 2011", U.S. Appl. No. 12/197,044, 11 pages.
U.S. Patent and Trademark Office, "U.S. Notice of Final Rejection dated Jan. 4, 2012", U.S. Appl. No. 12/197,044, 6 pages.
U.S. Patent and Trademark Office, "U.S. Amendment/Request Reconsideration—After Non-Final Rejection dated Jan. 9, 2012", U.S. Appl. No. 12/197,061, 22 pages.
U.S. Patent and Trademark Office, "U.S. Final Rejection Office Action dated Apr. 25, 2012", U.S. Appl. No. 12/197,061, 13 pages.
U.S. Patent and Trademark Office, "U.S. Request for Continued Examination dated May 3, 2012", U.S. Appl. No. 12/197,044, 3 pages.
U.S. Patent and Trademark Office, "US Pre-Appeal Brief Request for Review and Arguments dated May 3, 2012", U.S. Appl. No. 12/197,044, 5 pages.
U.S. Patent and Trademark Office, "US Notice of Appeal dated Aug. 27, 2012", U.S. Appl. No. 12/197,044, 1 page.
U.S. Patent and Trademark Office, "US Notice of Appeal dated Aug. 27, 2012", U.S. Appl. No. 12/197,061, 1 page.
U.S. Patent and Trademark Office, "US Pre-Brief Conference Request dated Aug. 27, 2012", U.S. Appl. No. 12/9701,661, 5 pages.
U.S. Patent and Trademark Office, "U.S. Restriction/Election Requirement dated Sep. 20, 2012", U.S. Appl. No. 13/202,311, 12 pages.
U.S. Patent and Trademark Office, "US Pre-Brief Appeal Conference Decision dated Oct. 17, 2012", U.S. Appl. No. 12/197,061, 2 pages.

(56) References Cited

OTHER PUBLICATIONS

U.S. Patent and Trademark Office, "U.S. Response to Election / Restriction dated Nov. 19, 2012", U.S. Appl. No. 13/202,311, 12 pages.
U.S. Patent and Trademark Office, "U.S. Request for Continued Examination dated Dec. 14, 2012", U.S. Appl. No. 12/197,061, 19 pages.
U.S. Patent and Trademark Office, "U.S. Notice regarding Non-Compliant or Non-Responsive Amendment dated Jul. 5, 2013", U.S. Appl. No. 13/202,311, 2 pages.
U.S. Patent and Trademark Office, "U.S. Supplemental Response or Amendment to Notice regarding Non-Compliant or Non-Responsive Amendment dated Jul. 26, 2013", U.S. Appl. No. 13/202,311, 9 pages.
U.S. Patent and Trademark Office, "U.S. Non-Final Rejection dated Dec. 4, 2013", U.S. Appl. No. 13/202,311, 18 pages.
U.S. Patent and Trademark Office, "U.S. Non-Final Rejection Office Action dated Mar. 20, 2014", U.S. Appl. No. 12/197,061, 15 pages.
U.S. Patent and Trademark Office, "U.S. Response to Non-Final Office Action dated Jun. 4, 2014", U.S. Appl. No. 13/202,311, 15 pages.
U.S. Patent and Trademark Office, "U.S. Final Office Action", U.S. Final Office Action dated Jun. 20, 2014, U.S. Appl. No. 13/202,311, 20 pages.
U.S. Patent and Trademark Office, "U.S. Amendment and Response to Non-Final Office Action dated Jun. 20, 2014" for U.S. Appl. No. 12/197,061, 13 pages.
U.S. Patent and Trademark Office, "Non-Final Office Action dated Sep. 9, 2014" for U.S. Appl. No. 12/197,044, 13 pages.
U.S. Patent and Trademark Office, U.S. Response to Final Office Action dated Sep. 19, 2014, U.S. Appl. No. 13/202,311, 13 pages.
U.S. Patent and Trademark Office, "U.S. Amendment and Response to Non-Final Office Action dated Jan. 9, 2015" for for U.S. Appl. No. 12/197,044, 12 pages.
U.S. Patent and Trademark Office, "Final Office Action dated Jan. 29, 2015" for U.S. Appl. No. 12/197,044, 8 pages.
U.S. Patent and Trademark Office, "Amendment and Response to Final Office Action dated Apr. 29, 2015" for U.S. Appl. No. 12/197,044, 8 pages.
Boyes, Stephen G. et al., "Surface Modification of Positive Contrast Nanoparticle Agents with RAFT Polymers Towards the Targeted Imaging and Treatment of Cancer", ACS Symp. Series 1053, 2010, 65-101.
Dalgleish, et al., "The CD4 (T4) antigen is an essential component of the receptor for the AIDS retrovirus", Nature, 312, Nature, 312, 20/27, Dec. 1984, 763-767.
Epstein, et al., Nature, 318, 1985, 663.
Hashim, Arig I. et al., "Imaging pH and Metastasis", NMR Biomedicine 24, 2011, 582-591.
Rowe, Misty D. et al., "Tuning the Magnetic Resonance Imaging Properties of Positive Contrast Agent Nanoparticles by Surface Modification with RAFT Polymers", Langmuir, 25, 2009, 9487-9499.
Shepley, et al., Proc. Natl. Acad. Scl USA, 85, 1988, 7743.
Wies, et al., Nature, 333, 1988, 426.
Zola, , "Monoclonal Antibodies: Preparation and Use of Monoclonal Antibodies and Engineered Antibody Derivatives, Pring Verlag (Dec. 15, 2000; 1st edition)".
Shan et al., "Preparation of Poly(N-isopropylacrylamide)-Monolayer-Protected Gold Clusters: Synthesis Methods, Core Size, and Thickness of Monolayer," Macromolecules, 2003, pp. 4526-4533, vol. 36.
"Body Fluids," Boundless Anatomy and Physiology, retrieved online on Jul. 9, 2018 at www.courses.lumenlearning.com/boundless-ap/cjapter/body-fluids (15 pages).
Kim et al.,"Thermo- and pH-Responsive Hydrogel-Coated Gold Nanoparticles," Chem. Mater. 2004, pp. 3647-3651, vol. 16.
Van Vlerken et al., "Multi-functional polymeric nanoparticles for tumor-targeted drug delivery," Expert Opinion on Drug Delivery, 2006; 3(2), pp. 205-216.
U.S. Appl. No. 12/197,044, filed Aug. 22, 2008.
U.S. Appl. No. 14/580,827, filed Dec. 23, 2014.
Song, et al., "Influence of Tumor pH on Therapeutic Response," Cancer Drug Resistance, 2006, Chapter 2, pp. 21-42.

* cited by examiner (a)

(b)

(c)

GOLD/LANTHANIDE NANOPARTICLE CONJUGATES AND USES THEREOF

CROSS REFERENCE TO RELATED APPLICATIONS

This application is a divisional application of U.S. patent application Ser. No. 13/202,311, filed Aug. 18, 2011, and entitled Gold/Lanthanide Nanoparticle Conjugates and Uses Thereof," which is a 371 National Phase application of International Application No. PCT/US2010/024450, filed Feb. 17, 2010, and entitled "Gold/Lanthanide Nanoparticle Conjugates and Uses Thereof," which claims priority to U.S. Patent Application No. 61/153,553 filed Feb. 18, 2009, and entitled "Gold/Lanthanide Nanoparticle Conjugates and Uses Thereof", each of which is hereby incorporated by reference in its entirety.

This application is related to U.S. patent application Ser. No. 12/197,044 filed Aug. 22, 2008, and entitled "Gold Nanoparticle Conjugates and Uses Thereof," and U.S. patent application Ser. No. 12/197,061 filed Aug. 22, 2008, entitled "Lanthanide Nanoparticle Conjugates and Uses Thereof", each of which is hereby incorporated by reference in its entirety.

FIELD

The disclosure generally relates to multimodal imaging agents. Specifically, this disclosure relates to gold/lanthanide nanoparticles with and without polymers grafted to, or polymerized from, the surface of lanthanide, e.g. gadolinium, nanoparticles. The polymers have functional groups that may be derivativized to include imaging agents, therapeutic agents, and targeting agents at their surface. Use of these multimodal nanoparticles will allow targeted delivery of imaging agents, and therapeutic compounds to specific cells, tissues, and organs.

BACKGROUND

Nanomedicine, according to the National Institutes of Health, refers to highly specific medical intervention at the molecular scale for diagnosis, prevention, and treatment of diseases. [Park, K. *J. Controlled Release* 2007, 120, 1-3]. One example nanomedicine is the use of nanodevices designed to image, target, and treat cancer.

Nanodevices could accomplish these disparate tasks through the use of agents or moieties associated with nanoparticles. The nanoparticles themselves may possess inherent capabilities (such as gadolinium nanoparticles used in to enhance magnetic resonance imaging or gold nanoparticles used to concentrate the energy of infrared lasers fo the thermoablation of cancer cells). Alternatively agents may be attached to the nanoparticle to provide specific capabilities such as antibodies directed against a specific tumor marker, or a chemotherapeutic compound attached to the nanoparticle.

Intravascularly injectable nanodevices (referred to as "theragnostic devices") are being developed for the treatment of cancer. However, there are problems with present manufacturing techniques for theragnostic devices. These manufacturing problems lead to poor loading efficiencies, low loading capacity, and the inability to control nanodevice production parameters such as size distribution, surface interactions, and in vivo performance. [Park, K. *J. Controlled Release* 2007, 120, 1-3]. Current design limitations also impact flexibility in choosing the type and quantity of incorporated moiety (drug and/or targeting agent). Another problem with the development of nanodevices is the lack of control over spatial orientation and architecture of the nanoparticle. Finally, nanodevices suffer from instability of the drug and/or targeting agent associated with the nanoparticle.

Multimodal imaging agents have the potential to overcome many of the limitations of current clinical imaging agents by providing a route to achieve diagnostic imaging, targetting, and therapy with administration of a single nanodevice. Combining these different capablities will reduce patient anxiety and discomfort.

Against this backdrop, the present disclosure has been developed

SUMMARY

The present disclosure is directed generally to gold/lanthanide nanoparticle conjugates, such as gold/gadolinium nanoparticle conjugates, nanoparticle conjugates including polymers, conjugation to targeting agents and therapeutic agents, and their use in targeting, treating, and/or imaging disease states in a patient. In certain embodiments, the gold/gadolinium nanoparticle conjugates are multifunctional polymeric systems. Biocompatible polymer backbones that can be conjugated to imaging agents, targeting agents, and therapeutic agents are produced. Post-polymerization modification of the polymer backbone allows attachment of targeting agents or therapeutic agents to a functional group. The resulting gadolinium nanoparticle conjugates provide the ability to target, treat, and image diseased cells.

In one aspect, gold/gadolinium nanoparticle conjugates are provided. The conjugate includes a gold nanoparticle coated with a gadolinium metal organic framework and a polymer or polymer precursor containing a functional group grafted to the nanoparticle. As used herein, polymer precursors include components of polymers, such as monomers, dimers, etc., or initiators bonded to the nanoparticle prior to polymerization. In various aspects, the functional group is selected from the group consisting of thiolates, thioethers, thioesters, carboxylates, amines, amides, halides, phosphonates, phosphonate esters, phosphinates, sulphonates, sulphates, porphyrins, nitrates, pyridine, pyridyl based compounds, nitrogen containing ligands, oxygen containing ligands, and sulfur containing ligands. In certain embodiments, the polymer, polymer precursor or initiator can be grafted onto the nanoparticle by a covalent or non-covalent bond between a functional group and nanoparticle. In certain embodiments, the functional group is a single thiol group and vacant orbital present on the gadolinium (III) cation. In further aspects, the gold/gadolinium nanoparticle conjugate can have the chemical structure according to Formula (I):

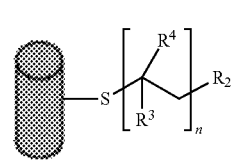

I wherein n is an integer;

$R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

In other embodiments, $R_2$ includes a functional group selected from thiolates, thioethers, thioesters, carboxylates, amines, amides, halides, phosphonates, phosphonate esters, phosphinates, sulphonates, sulphates, porphyrins, nitrates, pyridine, pyridyl based compounds, nitrogen containing ligands, oxygen containing ligands, and sulfur containing ligands.

The nanoparticle conjugate can further include a functional group. In certain variations, the functional group can be selected from carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives.

In other variations, the nanoparticle conjugate includes a therapeutic agent. In further variations, the nanoparticle further includes a targeting agent. Both the therapeutic agent and targeting agent are bonded to the polymer, optionally they are bonded to the polymer via a covalent linker or functional group.

In another aspect, the disclosure is directed to a pharmaceutical composition comprising the gold/gadolinium nanoparticle conjugate as described herein, and a pharmaceutically acceptable carrier.

In a further aspect, the disclosure is directed to methods of making nanoparticle conjugates. A nanoparticle having a suitable initiator is contacted with a dithioester, xanthate, or dithiocarbamate of Formula (II) or a trithiocarbonate of Formula (III):

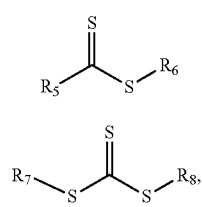

wherein
$R_5$, $R_6$, $R_7$, and $R_8$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

In other embodiments, $R_6$ and $R_8$ are each independently selected from a dithioester, xanthate, dithiocarbamate and trithiocarbonate to form a nanoparticle conjugate with the compounds of Formulae (II) or (III). Alternatively, the polymer or polymer precursor can be treated with a reducing agent to the compound of Formulae (II) or (III) before contacting said gold/gadolinium nanoparticle with said compound of formula (II) or (III).

In further aspects, the disclosure is directed to a method of treating a disease or disorder by administering a gold/gadolinium nanoparticle conjugate to a patient in need of treatment of said disease or disorder. In various embodiments, the targeting agent localizes the nanoparticle conjugate to the site of the disease or disorder. The therapeutic agent treats said disease or disorder. The method can be further combined with imaging the nanoparticle conjugate at the disease location.

BRIEF DESCRIPTION OF THE DRAWINGS

The disclosed Figures are exemplary, and are not intended to be limiting of the claims.

DETAILED DESCRIPTION

Figure 1:
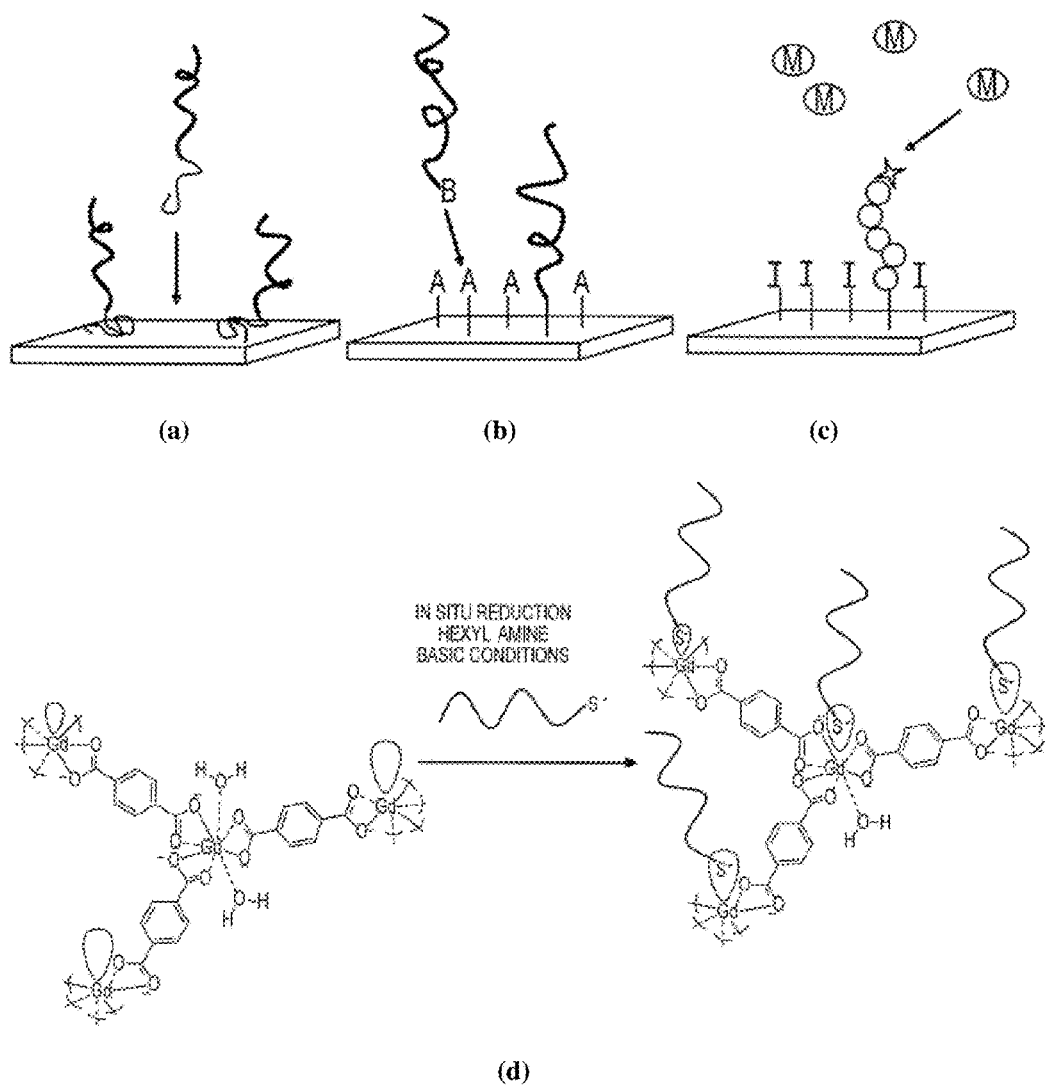
FIG. 1 depicts preparation of polymer modified surfaces by the (a) physisorption, (b) 'grafting to', and (c) 'grafting from' methods, (d) depicts a proposed coordination mechanism attachment of thiolate polymer chain ends to MOFs of Gd nanoparticles (NPs) synthesized by a reverse microemulsion system employing the 1,4-BDC ligand.

There has been an increasing focus on the development of multifunctional nanomedicines for improvement in the remedial results of drug treatment for cancer patients. See, e.g., Kukowska-Latallo, et al., *Cancer Res.* 2005, 65, 5317-5324. Sau, T. K. et al., *Langmuir* 2004, 20, 6414-6420; and Niidome, T. et al., *Journal of Controlled Release* 2006, 114, 343-347. Multifunctional nanomedicines incorporate diagnostic imaging capabilities, targeting through biomolecular recognition, and a therapeutic agent for treatment of a specific disease, providing a "one dose" approach of overcoming downfalls of conventional treatment and imaging techniques.

The disclosure relates to nanoparticles having both gold and gadolinium. In various aspects, the nanoparticles have application as multimodal, targeting, imaging, and/or therapeutic agents for the diagnosis and treatment of specific diseases. The gadolinium can act as a positive contrast agent for magnetic resonance imaging (MRI), and the gold nanoparticle can be used, for example, in computed X-Ray tomography (CT) as well as optical and dark field confocal microscopy. The gold nanoparticle may also be used to thermally ablate tumor cells with infrared, near-infrared light, or other wavelength energy. Furthermore, these nanoparticles have been surface modified with polymers prepared by reversible addition-fragmentation chain transfer (RAFT) polymerization that contain fluorescent monomers to enable fluorescence imaging of the modified particles. Using the previously disclosed procedure for modifying gadolinium nanoparticles with RAFT polymers, cancer targeting ligands, such as folic acid and G-RGD sequences, and cancer therapeutics, such as methotrexate, doxorubicin, and paclitaxel, can be added to the surface of the nanoparticles to enable the targeted imaging and treatment of various cancers.

The gold nanoparticle is coated with a gadolinium metal organic framework by disposing the gadolinium metal organic framework on or onto the gold nanoparticle. The interaction between the gold nanoparticle and the metal organic framework may include covalent as well as noncovalent interations. Without being limited by examples the interactions between the nanoparticle and metal organic framework may be ionic, hydrogen bonding, dipole-dipole, and Van der Waals forces.

Definitions

A dash ("-") that is not between two letters or symbols is used to indicate a point of attachment for a moiety or substituent. For example, —CONH$_2$ is attached through the carbon atom.

"Acyl" by itself or as part of another substituent refers to a radical —C(O)R$_{30}$, where R$_{30}$ is hydrogen, alkyl, cycloalkyl, cycloheteroalkyl, aryl, arylalkyl, heteroalkyl, heteroaryl or heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" by itself or as part of another substituent refers to a radical —NR$^{31}$C(O)R$^{32}$, where R$^{31}$ and R$^{32}$ are independently hydrogen, alkyl, cycloalkyl, cycloheteroalkyl, aryl, arylalkyl, heteroalkyl, heteroaryl or heteroarylalkyl as defined herein. Representative examples include, but are not limited to formamido, acetamido and benzamido.

"Acyloxy" by itself or as part of another substituent refers to a radical —OC(O)R$^{33}$, where R$^{33}$ is alkyl, cycloalkyl, cycloheteroalkyl, aryl, arylalkyl, heteroalkyl, heteroaryl or heteroarylalkyl as defined herein. Representative examples include, but are not limited to acetoxy, isobutyroyloxy, benzoyloxy, phenylacetoxy and the like "Alkanyl" by itself or as part of another substituent refers to a saturated branched, straight-chain or cyclic alkyl radical derived by the removal of one hydrogen atom from a single carbon atom of a parent alkane. In some embodiments, an alkanyl group comprises from 1 to 20 carbon atoms. In other embodiments, an alkanyl group comprises from 1 to 10 carbon atoms. In still other embodiments, an alkanyl group comprises from 1 to 6 carbon atoms. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). In some embodiments, an alkenyl group comprises from 1 to 20 carbon atoms. In other embodiments, an alkenyl group comprises from 1 to 10 carbon atoms. In still other embodiments, an alkenyl group comprises from 1 to 6 carbon atoms. Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkoxy" by itself or as part of another substituent refers to a radical —OR$^{34}$ where R$^{34}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)—OR$^{36}$ where R$^{35}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Alkoxycarbonylamino" by itself or as part of another substituent refers to a radical —NR$^{36}$C(O)—OR$^{37}$ where R$^{36}$ represents an alkyl or cycloalkyl group and R$^{37}$ is alkyl, cycloalkyl, cycloheteroalkyl, aryl, arylalkyl, heteroalkyl, heteroaryl, heteroarylalkyl as defined herein. Representative examples include, but are not limited to, methoxycarbonylamino, tert-butoxycarbonylamino and benzyloxycarbonylamino.

"Alkoxycarbonyloxy" by itself or as part of another substituent refers to a radical —OC(O)—OR$^{38}$ where R$^{38}$ represents an alkyl or cycloalkyl group as defined herein. Representative examples include, but are not limited to, methoxycarbonyloxy, ethoxycarbonyloxy and cyclohexyloxycarbonyloxy.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

"Alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms.

"Alkylamino" means a radical —NHR where R represents an alkyl or cycloalkyl group as defined herein. In certain embodiments, an alkoxy group is $C_{1-18}$ alkoxy, in certain embodiments, $C_{1-12}$ alkoxy, in certain embodiments, $C_{1-8}$ alkoxy, in certain embodiments, $C_{1-6}$ alkoxy, in certain embodiments, C1-4 alkoxy, and in certain embodiments, C1-3 alkoxy. Representative examples include, but are not limited to, methylamino, ethylamino, 1-methylethylamino, cyclohexyl amino and the like.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. In some embodiments, an alkynyl group comprises from 1 to 20 carbon atoms. In other embodiments, an alkynyl group comprises from 1 to 10 carbon atoms. In still other embodiments, an alkynyl group comprises from 1 to 6 carbon atoms. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Amide derivatives" as used herein refer to compounds having the structure RC(O)NR'R". The R, R' and R" in amide derivatives can each independently be any desired substituent, including but not limited to hydrogen, halides, and substituted or unsubstituted alkyl, alkoxy, aryl or acyl groups. The amine or amide group can be used as the point of attachment to a therapeutic or targeting group, optionally via a linker. Examples of amines and amides include, but are not limited to, 2-(N,N-diethylamino)ethyl methacrylate, 2-(N,N-diethylamino)ethyl acrylate, N-[2-(N,N-dimethylamino)ethyl]methacrylamide, N-[3-(N,N-dimethylamino)propyl]acrylamide, diallylamine, methacryloyl-L-lysine, 2-(tert-butylamino)ethyl methacrylate, N-(3-aminopropyl) methacrylamide hydrochloride, 3-dimethylaminoneopentyl acrylate, N-(2-hydroxypropyl)methacrylamide, N-methacryloyl tyrosine amide, 2-diisopropylaminoethyl methacrylate, 3-dimethylaminoneopentyl acrylate, 2-aminoethyl methacrylate hydrochloride, hydroxymethyldiacetoneacrylamide, N-(iso-butoxymethyl)methacrylamide and N-methylolacrylamide.

"Amine derivatives" are compound or radicals thereof having a functional group containing at least one nitrogen, and having the structure RNR'R". R, R' and R" in amine derivatives can each independently be any desired substituent, including but not limited to hydrogen, halides, and substituted or unsubstituted alkyl, alkoxy, aryl or acyl groups.

"Anhydride derivatives" as used herein refer to a compound or radical having the chemical structure R1C(O)OC (O)R2. The carboxyl groups, optionally after removal of $R^1$ or $R^2$ groups, can be used as the point of attachment to a therapeutic or targeting group, optionally via a linker. Examples of anhydride derivatives include, but are not limited to, acrylic anhydride, methacrylic anhydride, maleic anhydride, and 4-methacryloxyethyl trimellitic anhydride "Antibody" refers to a monomeric or multimeric protein comprising one or more polypeptide chains that binds specifically to an antigen. An antibody can be a full length antibody or an antibody fragment.

"Antibody, full length antibody," herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, $C_{H1}$ (Cγ1), $C_{H2}$ (Cγ2), and $C_{H3}$ (Cγ3). In some mammals, for example in camels and llamas, IgG antibodies may consist of only two heavy chains, each heavy chain comprising a variable domain attached to the Fc region.

"Antibody fragments" are portions of full length antibodies that bind antigens. Specific antibody fragments include, but are not limited to, (i) the Fab fragment consisting of $V_L$, $V_H$, $C_L$ and $C_H$, domains, (ii) the Fd fragment consisting of the $V_H$ and $C_{H1}$ domains, (iii) the Fv fragment consisting of the $V_L$ and $V_H$ domains of a single antibody; (iv) the dAb fragment (Ward et al., 1989, *Nature* 341:544-546) which consists of a single variable, (v) isolated CDR regions, (vi) F(ab')2 fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site (Bird et al., 1988, *Science* 242:423-426, Huston et al., 1988, *Proc. Natl. Acad. Sci. U.S.A.* 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). In certain embodiments, antibodies are produced by recombinant DNA techniques. Other examples of antibody formats and architectures are described in Holliger & Hudson, 2006, *Nature Biotechnology* 23(9):1126-1136, and Carter 2006, *Nature Reviews Immunology* 6:343-357 and references cited therein, all expressly incorporated by reference. In additional embodiments, antibodies are produced by enzymatic or chemical cleavage of naturally occurring antibodies.

"Aromatic Ring System" by itself or as part of another substituent refers to an unsaturated cyclic or polycyclic ring system radical having a conjugated TC electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group is from 6 to 20 carbon atoms. In other embodiments, an aryl group is from 6 to 12 carbon atoms.

"Arylalkyl" by itself or as part of another substituent refers to an acyclic alkyl radical in which one of the hydrogen atoms bonded to a carbon atom, typically a terminal or sp3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In other embodiments, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryloxy" refers to a radical —C—O-aryl where aryl is as defined herein.

"Aryloxycarbonyl" refers to a radical —C(O)—O-aryl where aryl is as defined herein.

"Azide derivatives" as used herein refer to a compound or a radical thereof having the structure N═N═N. The azide group can be used as the point of attachment to a therapeutic or targeting group, optionally via a linker. Examples of azide derivatives include, but are not limited to, 2-hydroxy-3-azidopropyl methacrylate, 2-hydroxy-3-azidopropyl acrylate, 3-azidopropyl methacrylate.

"Carbamoyl" by itself or as part of another substituent refers to the radical —C(O)NR$^{39}$R$^{40}$ where R$^{39}$ and R$^{40}$ are independently hydrogen, alkyl, cycloalkyl or aryl as defined herein.

"Carbamoyloxy" by itself or as part of another substituent refers to the radical —OC(O)NR$^{41}$R$^{42}$ where R$^{41}$ and R$^{42}$ are independently hydrogen, alkyl, cycloalkyl or aryl as defined herein.

"Carbazole derivatives" as used herein refer to a compound or radical thereof having the structure

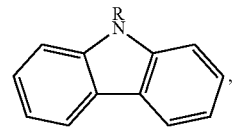

and any substitutions at any site thereof. The carbazole group can be used as the point of attachment to a therapeutic or targeting group, optionally via a linker. Examples of carbazole derivatives include but are not limited to, N-vinylcarbazole.

"Carboxylate" refers to a compound or radical thereof having the structure RCOO—, where R can be any desired substitutent.

"Compounds" include, but are not limited to, optical isomers of compounds, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds can include Z- and E-forms (or cis- and trans-forms) of compounds with double bonds.

"Compounds" may also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{10}$C, $_{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides of a Formula. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Compounds" as defined by a chemical formula as disclosed herein include any specific compounds within the formula. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

"Conjugate acid of an organic base" refers to the protonated form of a primary, secondary or tertiary amine or heteroaromatic nitrogen base. Representative examples include, but are not limited to, triethylammonium, morpholinium and pyridinium.

"Covalent grafting" as used herein refers to attaching a polymer, polymer precursor, or small molecule by one or more covalent bonds from a functional group to the surface of a nanoparticle or by a delocalized bond complex, such as a delocalized bond complex.

"Cyano derivatives" as used herein refer to compounds or radicals thereof having the structure RCN. R can each independently be any desired substituent. The cyano group can be used as the point of attachment to a therapeutic or targeting group, optionally via a linker. Examples of cyano derivatives include, but are not limited to, 2-cyanoethyl acrylate.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In some embodiments, the cycloalkyl group is $(C_3-C_{10})$ cycloalkyl. In other embodiments, the cycloalkyl group is $(C_3-C_7)$ cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino" by itself or as part of another substituent refers to the radical —$NR^{43}R^{44}$ where $R^{43}$ and $R^{44}$ are independently alkyl, cycloalkyl, cycloheteroalkyl, arylalkyl, heteroalkyl or heteroarylalkyl, or optionally $R^{43}$ and $R^{44}$ together with the nitrogen to which they are attached form a cycloheteroalkyl ring.

"Epoxide derivatives" as used herein refer to compounds or radicals thereof having the following chemical structure:

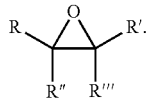

"Ester derivatives" as used herein refer to a compound or a radical thereof having the generic chemical structure RC(O)OR'. R and R' can each independently be any desired substituent. The ester group can be used as the point of attachment to a therapeutic or targeting group, optionally via a linker. Examples include, but are not limited to, methyl acrylate, methyl methacrylate, tert-butyl acrylate, tert-butyl methacrylate, vinyl acetate, benzyl acrylate and benzyl methacrylate.

"Ether derivatives" as used herein refer to a compound or a radical thereof having the generic chemical structure R—O—R'. The ether group can be used as the point of attachment to a therapeutic or targeting group, optionally via a linker. Examples include, but are not limited to, methyl vinyl ether, butyl vinyl ether, 2-chloroethyl vinyl ether, cyclohexyl vinyl ether.

"Grafting" or "grafted onto" as used herein refers to attaching a polymer, polymer precursor or small molecule to the surface of a nanoparticle via a single functional group. Grafting includes both covalent and non-covalent binding, as well as, but not limited to, delocalized bond formation between one or more atoms of the nanoparticle and one or more atoms of the functional group, ionic bonding, hydrogen bonding, dipole-dipole bonding, and van der Waals forces (for non-limiting examples see FIG. 1). Formation of exemplary bonds are depicted in Schemes 2 and 3 described herein. The terms "grafting" and "grafting onto" include methods conventionally referred to as grafting from and grafting to.

"Halide derivatives" as used herein refer to compounds or radicals thereof having a halide substituent. The halide group can be used as the point of attachment to a therapeutic or targeting group, optionally via a linker. Examples include, but are not limited to, vinyl chloride, 3-chlorostyrene, 2,4,6-tribromophenyl acrylate, 4-chlorophenyl acrylate, 2-bromoethyl acrylate. Non-limiting examples include, but are not limited to, divinylbenzene, ethylene glycol diacrylate, N,N-diallylacrylamide, and allyl methacrylate.

"Halo" means fluoro, chloro, bromo, or iodo radical.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —$NR^{45}R^{46}$, —N=N—, —N=N—$NR^{47}R^{48}$, —$PR^{49}$—, —$P(O)_2$—, —$POR^{50}$—, —O—$P(O)_2$—, —SO—, —$SO_2$—, —$SnR^{51}R^{52}$— and the like, where $R^{45}$, $R^{46}$, $R^{47}$, $R^{48}$, $R^{49}$, $R^{50}$, $R^{51}$ and $R^{52}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroalkyloxy" means an —O-heteroalkyl where heteroalkyl is as defined herein.

"Heteroaromatic Ring System" by itself or as part of another substituent refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Certain heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In other embodiments, the heteroarylalkyl group is a 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Heteroaryloxycarbonyl" refers to a radical —C(O)—OR where R is heteroaryl as defined herein.

"Hydroxyl derivative" as used herein refers to a compound or radical having the structure ROH. The deprotonated hydroxyl group can be used as the point of attachment to a therapeutic or targeting group, optionally via a linker. Example of hydroxyl derivatives include, but are not limited to, vinyl alcohol, 2-hydroxyethyl acrylate, 2-hydroxyethyl methacrylate, 2-allyl-2-methoxyphenol, divinyl glycol, glycerol monomethacrylate, poly(propylene glycol) monomethacrylate, N-(2-hydroxypropyl)methacrylamide, hydroxymethyldiacetoneacrylamide, poly(ethylene glycol) monomethacrylate, N-methacryloylglycylglycine, N-methacryloylglycyl-DL-phenylalanylleucylglycine, 4-methacryloxy-2-hydroxybenzophenone, 1,1,1-trimethylolpropane diallyl ether, 4-allyl-2-methoxyphenol, hydroxymethyldiacetoneacrylamide, N-methylolacrylamide, and sugar based monomers.

"Maleimide derivative" as referred to herein refers to a compound or a radical thereof having the structure:

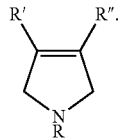

"Morpholine derivatives" as used herein refer to compounds or radicals thereof having the structure:

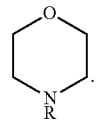

Typically, the amine group serves as the point of attachment to other compounds. The morpholine group can be used as the point of attachment to a therapeutic or targeting group, optionally via a linker. Examples of morpholine derivatives include, but are not limited to, N-acryloylmorpholine, 2-N-morpholinoethyl acrylate and 2-N-morpholinoethyl methacrylate.

"Nitro derivatives" as used herein refer to compounds or radicals thereof having an NO2 group. The nitro group can be used as the point of attachment to a therapeutic or targeting group, optionally via a linker. Examples include, but are not limited to, o-nitrobenzyl methacrylate, methacryloylglycyl-DL-phenylalanyl-L-leucyl-glycine 4-nitrophenyl ester, methacryloylglycyl-L-phenylalanyl-L-leucyl-glycine 4-nitrophenyl ester, N-methacryloylglycylglycine 4-nitrophenyl ester, 4-nitrostyrene "Patient" includes animals and mammals, such as for example, humans.

"Pharmaceutical composition" refers to a compound or nanoparticle at least one pharmaceutically acceptable vehicle, with which the compound or nanoparticle is administered to a patient "Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound. "Phosphate derivatives" as used herein refer to compounds or radicals thereof having at least one compound containing the structure RR'R"PO$_4$. R, R' and R" can each independently be any desired substituent, including but not limited to hydrogen, alkyl, alkoxy, aryl or acyl groups. The phosphate group can be used as the point of attachment to a therapeutic or targeting group, optionally via a linker. Examples of phosphate derivatives include, but are not limited to, monoacryloxyethyl phosphate and bis(2-methacryloxyethyl) phosphate.

"Phosphinate" refers to a compound or radical thereof having the structure OP(OR)R'R" where R, R' and R' can each independently be any desired substituent.

"Phosphonate" refers to a compound or radical thereof having the structure R—PO(OH)$_2$ or R—PO(OR')$_2$, where R and R' can each independently be any desired substituent.

"R, R' and R"" can each independently be any desired substituent.

"R, R', R", and R'"" can each independently be any desired substituent. The epoxide group can be used as the point of attachment to a therapeutic or targeting group, optionally via a linker. Examples of epoxide derivatives include, but are not limited to, glycidyl methacrylate.

"Reducing agent" is an element or a compound that reduces another species.

Exemplary reducing agents include, but are not limited to, ferrous ion, lithium aluminium hydride (LiAlH$_4$), potassium ferricyanide (K$_3$Fe(CN)$_6$), sodium borohydride (NaBH$_4$), sulfites, hydrazine, diisobutylaluminum hydride (DIBAH), primary amines, and oxalic acid (C$_2$H$_2$O$_4$).

"Salt" refers to a salt of a compound, including, but not limited to, pharmaceutically acceptable salts.

"Silane derivative" as used herein refers to compounds or radicals thereof having at least one substituent having the structure RSiR'R"R'". R, R' and R" can each independently be any desired substituent, including but not limited to hydrogen, alkyl, alkoxy, aryl or acyl groups. The silane group can be used as the point of attachment to a therapeutic or targeting group, optionally via a linker. Examples of silane derivatives include, but are not limited to, 3-methacryloxypropyl trimethoxysilane, vinyltriethoxysilane, 2-(trimethylsiloxy)ethyl methacrylate, 1-(2-trimethylsiloxy-ethoxy)-1-trimethylsiloxy-2-methylpropene "Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Substituted" refers to a group in which one or more hydrogen atoms are each independently replaced with the same or different substituent(s). Typical substituents include, but are not limited to, —X, —R$^{29}$, —O—, =O, —OR$^{29}$, —SR$^{29}$, —S—, =S, —NR$^{29}$R$^{30}$, =NR$^{29}$, —CX$_3$, —CF$_3$, —CN, —OCN, —SCN, —NO, —NO$_2$, =N$_2$, —N$_3$, —S(O)$_2$O—, —S(O)$_2$OH, —S(O)$_2$R$^{29}$, —OS(O)$_2$O—, —OS(O)$_2$R$^{29}$, —P(O)(O—)$_2$, —P(O)(OR$^{29}$)(O—), —OP(O)(OR$^{29}$)(OR$^{30}$), —C(O)R$^{29}$, —C(S)R$^{29}$, —C(O)OR$^{29}$, —C(O)NR$^{29}$R$^{30}$, —C(O)O—, —C(S)OR$^{29}$, —NR$^{31}$C(O) NR$^{29}$R$^{30}$, —NR$^{31}$C(S)NR$^{29}$R$^{30}$, —NR$^{31}$C(NR$^{29}$)NR$^{29}$R$^{30}$ and —C(NR$^{29}$)NR$^{29}$R$^{30}$, where each X is independently a halogen; each R$^{29}$ and R$^{30}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{31}$R$^{32}$, —C(O)R$^{31}$ or —S(O)$_2$R$^{31}$ or optionally R$^{29}$ and R$^{30}$ together with the atom to which they are both attached form a cycloheteroalkyl or substituted cycloheteroalkyl ring; and R$^{31}$ and R$^{32}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Succinimide derivative" as used herein refers to compounds or radicals thereof having the group

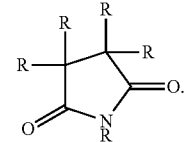

The succinyl R groups can be substituted by any substituent, for example and substituted or unsubstituted alkyl, alcoxy, aryl groups. Typically, the succinimide group is attached to a compound via a covalent bond at the nitrogen. The succinimide group can be used as the point of attachment to a therapeutic or targeting group, optionally via a linker. A succinimide derivative can be a sulfo-containing succinimide derivative. N-acryloxysuccinimide is an exemplary succinimide derivative.

"Sulfonamido" by itself or as part of another substituent refers to a radical —NR$^{53}$S(O)$_2$R$^{54}$, where R$^{53}$ is alkyl, substituted alkyl, cycloalkyl, cycloheteroalkyl, aryl, substituted aryl, arylalkyl, heteroalkyl, heteroaryl or heteroarylalkyl and R$^{54}$ is hydrogen, alkyl, cycloalkyl, cycloheteroalkyl, aryl, arylalkyl, heteroalkyl, heteroaryl or heteroarylalkyl as defined herein. Representative examples include, but are not limited to methanesulfonamido, benzenesulfonamido and p-toluenesulfonamido.

"Sulfonic acids derivatives" as used herein are a class of organic acid radicals with the general formula RSO$_3$H or RSO$_3$. An oxygen, suflur, or R moiety can serve as a point of attachment. Sulfonic acid salt derivatives substitute a cationic salt (e.g. Na$^+$, K$^+$, etc.) for the hydrogen on the sulfate group. In various embodiments, the deprotonated sulfonic acid group can be used as the point of attachment to a therapeutic or targeting group, optionally via a linker. Examples of sulfonic acid derivatives and include, but are not limited to, 2-methyl-2-propane-1-sulfonic acid-sodium salt, 2-sulfoethyl methacrylate, 3-phenyl-1-propene-2-sulfonic acid-p-toluidine salt, 3-sulfopropyl acrylate-potassium salt, 3-sulfopropyl methacrylate-potassium salt, ammonium 2-sulfatoethyl methacrylate, styrene sulfonic acid, 4-sodium styrene sulfonate.

"Sulphate" refers to a compound or radical thereof having the structure $RSO_4$, where R can be any desired substituent.

"Sulphonate" refers to a compound or radical thereof having the structure $RSO_2O$— where R can be any desired substituent.

"Therapeutically effective amount" or "effective amount" refers to the amount of a compound that, when administered to a subject for treating a disease or disorder, or at least one of the clinical symptoms of a disease or disorder, is sufficient to affect such treatment of the disease, disorder, or symptom. The "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate therapeutically effective amount in any given instance may be ascertained by those skilled in the art or capable of determination by routine experimentation.

"Therapeutically effective dose" or "effective dose" refers to a dose of a drug, prodrug or active metabolite of a prodrug that provides effective treatment of a disease or disorder in a patient. A therapeutically effective dose may vary from compound to compound and from patient to patient, and may depend upon factors such as the condition of the patient and the route of delivery. A therapeutically effective dose may be determined in accordance with routine pharmacological procedures known to those skilled in the art.

"Thioester" refers to a compound or radical thereof having the structure R—S—CO—R', where R and R' can each independently be any desired substituent.

"Thioether" refers to a compound or radical thereof having the structure R—S—CO—R', where R and R' can each independently be any desired substituent.

"Thiolate" refers to a compound or radical thereof having a —SR structure, where R can be any desired substituent.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease, disorder, or at least one of the clinical symptoms of a disease or disorder. "Treating" or "treatment" also refers to inhibiting the disease, disorder, or at least one of the clinical symptoms of a disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder. Nanoparticles The present disclosure is directed to modified gold/lanthanide nanoparticles, particularily gold/gadolinium nanoparticles. The term "nanoparticle" as referred to herein means a particle having at least one special dimension measurable less than a micron in length. Nanoparticles include conventionally known nanoparticles such as nanorods, nanospheres and nanoplatelets. In various embodiments, for example, nanospheres can be a rod, sphere, or any other three dimensional shape. Nanoparticles are generally described, for example, in Burda et al., *Chem. Rev.* 2005, 105, 1025-1102.

The nanoparticles described herein are generally described as gold/lanthanide nanoparticles, such as gold/gadolinium nanoparticles. However, the descriptions provided herein may be applied equally and fully to other lanthanide nanoparticles. In this context, lanthanides include gadolinium, lanthanum, erbium, ytterbium, neodymium, europium, terbium, cerium, thulium, praseodymium, promethium, samarium, dysprosium, holmium, and lutetium.

Gold Nanoparticles

Gold nanoparticles have architectures which provide tunable optical properties. In various embodiments, gold nanoparticles are configured for optical imaging techniques. For example, the optical and electronic properties can be controlled by controlling the size of the nanoparticle, varying the aspect ratio, or rationally assembling nanoparticles into a specific shape. Those of skill in the art will understand that the size of the gold nanoparticle can be designed to have specific properties for different applications. For example, the size of the gold nanoparticle can be designed for colorimeric detection, as described in Martin and Mitchell, *Anal. Chem.* 1998 pp. 332. Additionally, due to their tunable optical properties, multifunctional polymer modified gold and ultrasensitive surface-enhanced Raman detection of biomolecules such as DNA and cancer markers. Metallic gold nanoparticles with surface plasmon behavior have been used as unique optical probes for colorimetric sensing and ultrasensitive surface-enhanced Raman detection of biomolecules such as DNA and cancer markers. Cheon, J. and Lee, Jae-Hyun, Synergistically Integrated Nanoparticles as Multimodal Probes for Nanobiotechnology, *Accounts of Chem. Res.*, published online at www.pubs.acs.org/acr on Aug. 13, 2008.

Gold nanoparticles may be prepared by methods known in the art, including those disclosed by Burda et al., *Chem. Rev.* 2005, 105, 1025-1102 and Daniel and Astruc *Chem. Rev.* 2004, 104, 293-346. Growth methods, including the template, electrochemical, or seeded growth methods, are disclosed by Pérez-Juste et al., *Coordination Chemistry Reviews* 249 (2005) 1870-1901. Seed particle methods are further described in Murphy et al. *J. Phys. Chem. B* 2005, 109, 13857-13870. Gold nanoparticles can also be prepared to have specific surface structures by citrate reduction, two phage synthesis and thiol stabilization, sulfur stabilization, and stabilization with other ligands as described by Daniel and Astruc, *Chem. Rev.* 2004, 104, 293-346.

Gadolinium Metal Organic Framework

Gadolinium (III) functions as a MRI contrast agent. Gadolinium enhances the image contrast by increasing water proton relaxation rates. When conjugated to targeting agents, gadolinium metal organic frameworks are effective site-specific MRI contrast agents owing to their large metal payload.

"Gadolinium metal organic framework" as used herein refers to a metal organic framework containing gadolinium (III) $Gd^{3+}$. Gadolinium metal organic frameworks include, but are not limited to, gadolinium (III) metal-organic frameworks such as those containing carboxylic acids, ligands, and polymers. Representative examples of gadolinium (III) metal organic frameworks include Gd(1,4-benzenedicarboxylate)1.5$(H_2O)_2$ (also known as Gd(1,4-BDC)1.5 $(H_2O)_2$), $Gd_2O_3$, gadolinium nitrate and emulsions thereof, and gadolinium fluoride.

Gadolinium metal organic frameworks can be synthesized by any method known in the art. In a certain embodiment, the gadolinium particles are synthesized as described in, e.g., Rieter, W. J.; et al. *J. Am. Chem. Soc.* 2006, 128, 9024-9025. The quantity of gadolinium (III) in gadolinium metal organic frameworks can be controlled as described in the art by controlling reaction conditions. Rieter, W. J. et al., *J. Am. Chem. Soc.* 2006 128, 9024-9025.

In alternative embodiments, gadolinium nanoparticles can be synthesized to have a shell morphology with a functionalized polymer on the surface. For example, gadolinium nanoparticles having a paramagnetic $Gd_2O_3$ core can be produced by encapsulating $Gd_2O_3$ cores within a polysiloxane shell which carries organic fluorophores and carboxylated PEG covalently tethered to the inorganic network as described in Bridot et al., *J. Am. Chem. Soc.*; (Article); 2007; 129(16); 5076-5084. In other embodiments, the gadolinium nanoparticles can be synthesized as inorganic/organic hybrid molecules, as described in Hifumi et al. *J. Am. Chem. Soc.*, 128 (47), 15090-15091, 2006.

The quantity of gadolinium in a gadolinium metal organic framework can be modified to adjust contrast in MRI techniques. For example, the quantity of gadolinium in a gadolinium nanoparticle can be optimized for imaging techniques such as magnetic resonance imaging (MRI). The quantity of gadolinium nanoparticles can be adjusted for, for example, in Ahrens et al., *Proc. Nat'l. Acad. Sci.* 95(15) 8443-8448 (1998). Various parameters of gadolinium nanoparticles can be modified. Parameters include the concentration of gadolinium (III), size, aspect ratio, and surface-to-volume concentration of gadolinium (III) in the nanoparticle as described in e.g. Rieter, W. J. et al., *J. Am. Chem. Soc.* 2006 128, 9024-9025.

Gadolinium Coated Gold Nanoparticles

A gadolinium organic framework is deposited on the gold nanoparticle. The metal organic framework may be attached to the gold nanoparticle via covalent, noncovalent, ionic, Van der Waals, or other types of bonds.

A reverse microemulsion reaction is used to coat gold nanoparticles with gadolinium metal organic frameworks (NMOF). In one embodiment two aqueous solutions are prepared, one of $GdCl_3$ (0.5M) and the other containing 1,4-benzenedicarboxylic acid (1,4-BDC) (0.075M). Next, the $GdCl_3$ and 1,4-BDC aqueous solutions are combined into a heptane/hexanol/cetyltrimethylammonium bromide (0.05M) microemulsion. Gold nanoparticles are then added to the solution and the reaction is stirred vigorously for 24 hours at room temperature. The nanoparticles are washed several times in ethanol and finally stored in water.

A polymer may be affixed to the metal organic framework. The polymer coating may be created either by polymerizing monomers from the surface of the metal organic framework, or by first polymerizing monomers and then attaching the resulting polymers to the metal organic framework (FIG. 1).

The polymer coating may be added directly to the metal organic framework via a a polymer precursor, or through an initiator, formed by creating imperfections on the metal organic framework.

Forming Initiators on the Nanoparticle Surface

Prior to growing polymers on the surface of gadolinium coated gold nanoparticles, the nanoparticle can be treated to form imperfections (or initiators) on the gadolinium metal organic framework surface. In various embodiments, initiators facilitate polymer formation or polymer precursor binding.

Polymerization

Polymerization can be performed by any method known in the art. Polymerization methods that can be used are described in *Principles of Polymerization,* 4th edition (2004) by George Odian, Published by Wiley-Interscience, which is incorporated herein by reference in its entirety. Various methods of polymerization include RAFT, Atom Transfer Radical Polymerization (ATRP), Stable Free Radical Polymerization (SFRP), and conventional free radical polymerization.

Reversible addition-fragmentation chain transfer (RAFT) polymerization operates on the principle of degenerative chain transfer. Without being limited to a particular mechanism, Scheme 1 shows a proposed mechanism for RAFT polymerization. In Scheme 1, RAFT polymerization involves a single- or multi-functional chain transfer agent (CTA), such as the compound of formula (I), including dithioesters, trithiocarbonates, xanthates, and dithiocarbamates. The initiator produces a free radical, which subsequently reacts with a polymerizable monomer. The monomer radical reacts with other monomers and propagates to form a chain, Pn*, which can react with the CTA. The CTA can fragment, either forming R*, which will react with another monomer that will form a new chain Pm* or Pn*, which will continue to propagate. In theory, propagation to the Pm* and Pn* will continue until no monomer is left or a termination step occurs. After the first polymerization has finished, in particular circumstances, a second monomer can be added to the system to form a block copolymer.

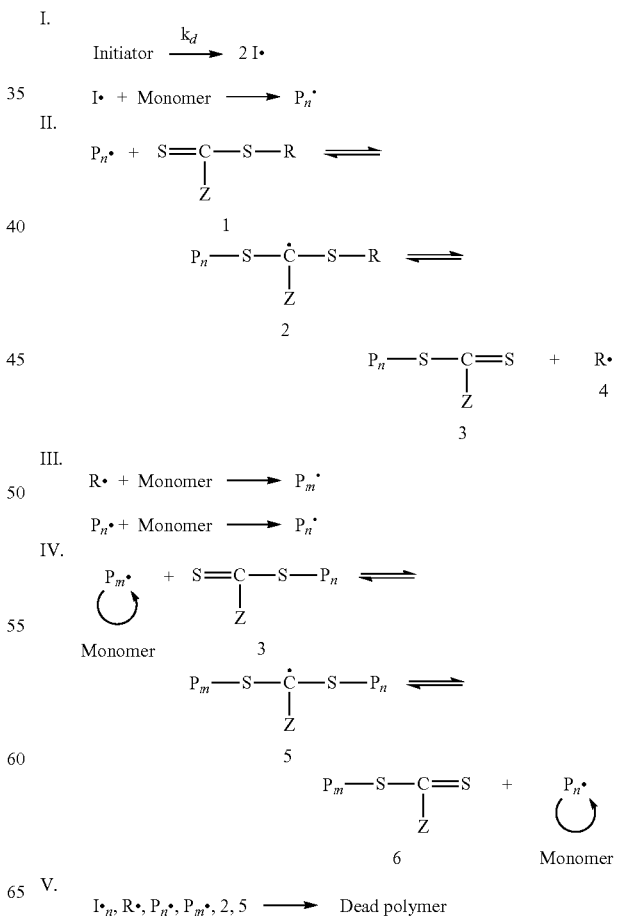

RAFT polymerization involves a similar mechanism as traditional free radical polymerization systems, with the difference of a purposely added CTA. Addition of a growing chain to a macro-CTA yields an intermediate radical, which can fragment to either the initial reactants or a new active chain. With a high chain transfer constant and the addition of a high concentration of CTA relative to conventional initiator, synthesis of polymer with a high degree of chain-end functionality and with well defined molecular weight properties is obtained.

In particular embodiments, RAFT polymerization is used to produce a variety of well-defined, novel polymers that either are polymerized from the surface of the metal organic framework, or are polymerized and then attached to the metal organic framework. RAFT polymerization shows great promise in the synthesis of multifunctional polymers due to the versatility of monomer selection and polymerization conditions, along with the ability to produce well-defined, narrow polydispersity polymers with both simple and complex architectures.

In particular embodiments, RAFT polymerization is used to produce a variety of well-defined, novel biocopolymers as constructs for multifunctional systems for the surface modification of nanoparticles consisting of gold nanoparticles coated in a metal organic framework (MOF) of gadolinium. The inherent flexibility of RAFT polymerizations makes it a candidate to produce well-defined polymer structures with a high degree of functionality capable of providing increased therapeutic/targeting agent loading and loading efficiency. For example, RAFT can be successfully used to produce well-defined activated biocopolymer constructs with N-acryloxysuccinimide (NAOS) pendant functionalities. The succinimide side groups have allowed covalent conjugation of bioactive agents such as fluorescent tags, nucleotides, peptides, and antibodies. R. P. Sebra, *Langmuir* 2005, 21, 10907-10911; M. J. Yanjarappa, *Biomacromolecules* 2006, 7, 1665-1670. Incorporation of NAOS into copolymers provides a route of manipulating loading efficiency and stability of bioactive agents. Additional tailoring of the copolymer conjugate system with tumor targeting or therapeutic agents allows specific localization and treatment to be achieved increasing in vivo performance.

Polymers synthesized by RAFT include chain transfer agents (CTAs). As used herein, a RAFT chain transfer agent is defined as having the chemical structure of Formula (IV):

(IV)

CTAs agents possessing the thiocarbonylthio moiety, impart reactivity to free-radical polymerization due to the facile nature of radical addition to C=S bonds which contributes to faster chain equilibration in the chain transfer step. The transfer constants of RAFT CTAs depend on the Z and R substituents. In certain embodiments, the Z group is a free radical stabilizing species to ensure rapid addition across the C=S bond.

In certain embodiments, the R group is chosen so that it possesses an equal or greater ability to leave as compared to the addition species. It is also of importance that the R group be able to reinitiate the polymerization after fragmentation.

In certain embodiments, R can fragment from the intermediate quickly and is able to re-initiate polymerization effectively.

Exemplary CTAs include, but are not limited to, cumyl dithiobenzoate (CDTB) and S-1-Dodecyl-S'-(α,α'-dimethyl-α"-acetic acid) trithiocarbonate (DATC).

Grafting Polymers and Polymer Precursors to Nanoparticles

In certain aspects, polymers can be grafted to the gadolinium metal organic framework after polymerization. Optimal choice of CTA structures of formula (I) allows for control of the polymerization. The Z group activates the thio-carbonyl (C=S) group for radical addition and allows for the radical intermediate to be stabilized in the transition state.

Schemes 2 and 3 show grafting trithiocarbonate and dithioester RAFT agents to the surface of a gadolinium nanoparticle. Scheme 2 shows first RAFT polymerization of the alkene in the presence of the trithiocarbonate, and Scheme 3 shows a first step of RAFT polymerization of the alkene in the presence of the dithioester.

The RAFT polymer is grafted to the surface of the nanoparticle. Without being limited to any particular mechanism, the nanoparticle is covalently grafted to the nanoparticle surface. The reduced polymer is covalently grafted to the nanoparticle.

Scheme 2

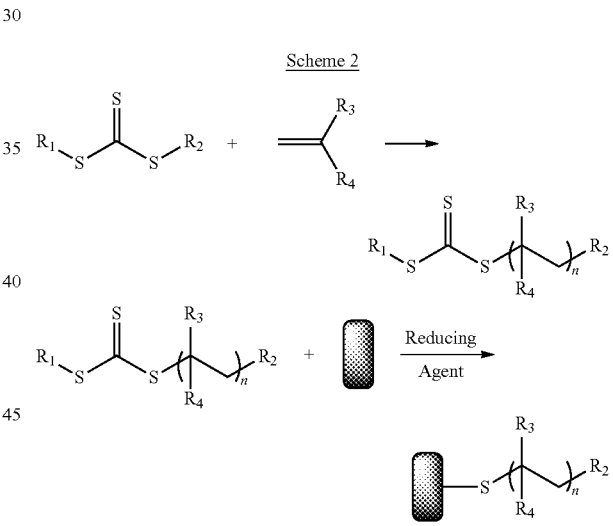

Scheme 3

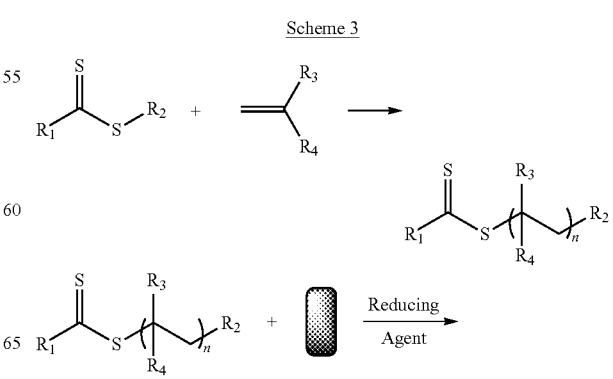

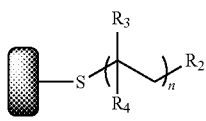

In Schemes 2 and 3, $R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

A specific example of RAFT polymers attached to the surface of the gadolinium particle after polymerization is depicted in Scheme 4 below.

The modified polymer can be added to the gadolinium nanoparticle after reduction of the trithiocarbonate group to a thiol to produce a gadolinium nanoparticle conjugate. Scheme 4 depicts a method of attaching a modified polymer to a gadolinium nanoparticle to produce a gadolinium nanoparticle conjugate.

Grafting from Nanoparticles

In the two examples of generalized RAFT polymerization described above in Schemes 2 and 3, as well as the specific example in Scheme 4, polymerization occurs prior to grafting to the gadolinium nanoparticle surfaces (i.e. "grafting to" the nanoparticle surface).

Alternatively, the RAFT polymerization may be accomplished after grafting a polymer precursor, initiator, or CTA to the nanoparticle surface. Scheme 5 depicts attachment of a CTA to a surface-bound RAFT polymerization. In brief, a polymer precursor is grafted to the surface of the nanoparticle. A CTA is attached to the terminus of the polymer precursor in Step 1. RAFT polymerization is then accomplished in Step 2 directly from the surface of the gadolinium nanoparticle, as described, for example, in Rowe-Konopacki, M. D. and Boyes, S. G. Synthesis of Surface Initiated Diblock Copolymer Brushes from Flat Silicon Substrates Utilizing the RAFT Polymerization Technique. *Macromolecules*, 40 (4) 879-888, 2007, and Rowe, M. D.; Hammer, B. A. G.; Boyes, S. G. Synthesis of Surface-Initiated Stimuli-Responsive Diblock Copolymer Brushes Utilizing a Combination of ATRP and RAFT Polymerization Techniques. *Macromolecules*, 41 (12), 4147-4157, 2008.

Scheme 5

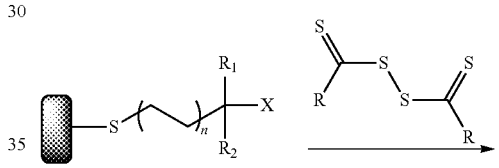

Scheme 4

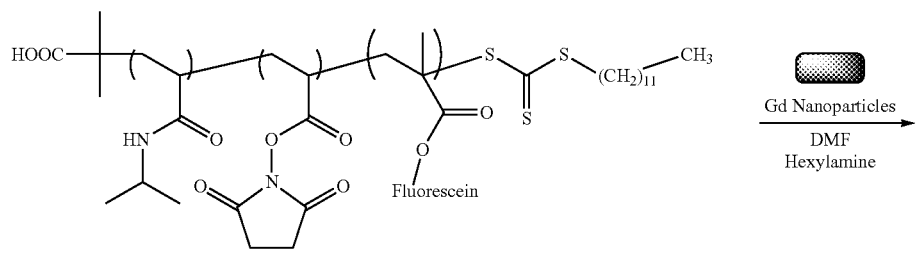

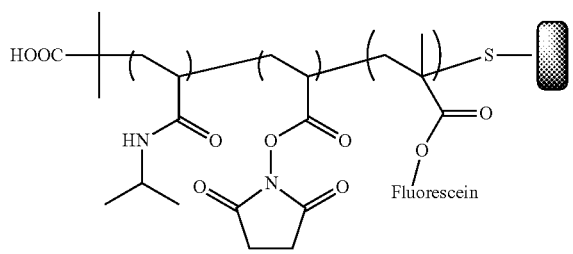

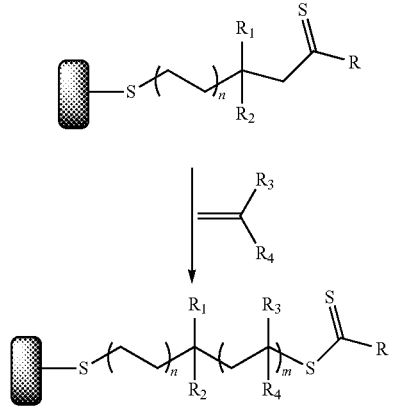

In Scheme 5, n is an integer, and X, R, $R_1$, $R_2$, $R_3$ and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy. In certain embodiments, X is a halide such as fluorine, bromine, chlorine and iodine. A specific example of the reaction of Scheme 5 is depicted in Scheme 6.

Scheme 6

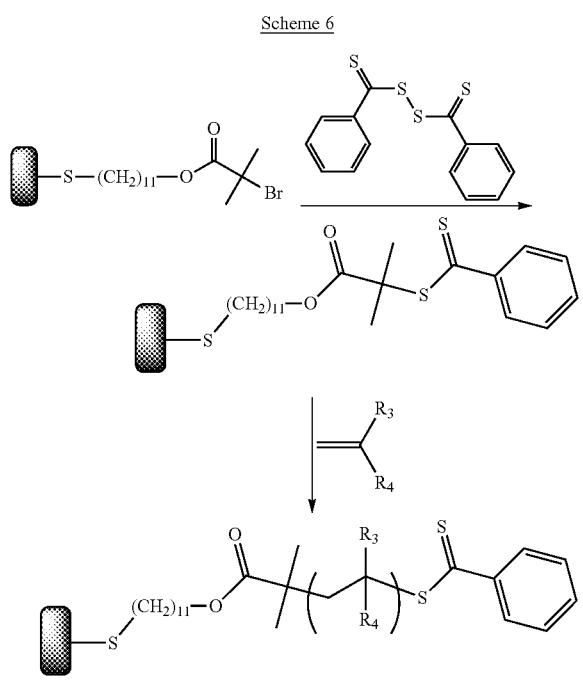

$R_3$ and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

Figure 2:
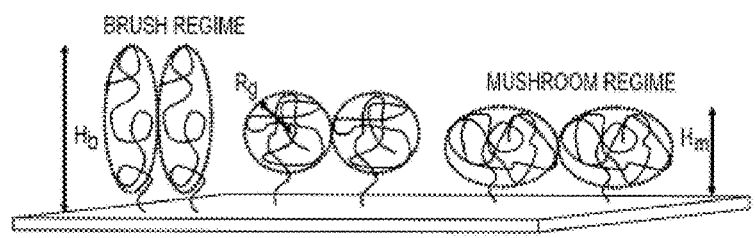
FIG. 2 depicts the mushroom to brush spatial transition of polymers at a surface.

Grafting from the surface of the nanoparticle as depicted above allows formation of a "brush" configuration of polymers. With reference to FIG. 2, polymers attached to a gadolinium surface can be spaced differently on a surface. Without wishing to be held to a specific theory or mechanism of action, the accessibility of the therapeutic agents and targeting agents to the surrounding environment can be at least partially controlled by how closely together the polymers are spaced on the surface of the nanoparticle. When the distance between the polymers is greater than the length of the polymer, the polymers adopt a "mushroom" configuration in which the entirety of the polymer can be accessible to surrounding environment, including the binding site of a targeting agent or therapeutic agent attached to the polymer. Conversely, when the distance between the polymer chains is shorter than the attached polymer, the polymers have a brush conformation, in which the terminal portions of the polymer are accessible to the surrounding environment. If the therapeutic and/or targeting agents are attached to the terminus of the polymers arranged in a "brush" conformation, then the therapeutic and/or targeting agents can be accessible to the surrounding environment.

Desired polymer configuration on the surface can be achieved by growing the polymers from the surface of the nanoparticle. In certain aspects, the polymerization is initiated directly from substrate via immobilized initiators. The brush polymer conformation can be achieved by forming the polymer from the nanoparticle surface, or alternatively by utilizing separately or combining atom transfer radical polymerization (ATRP) and RAFT polymerization. Growing the polymers from the surface allows immobilized polymerization initiators to be tailored for a wide range of polymerization techniques and substrates.

In particular, synthesizing polymer brushes requires control of the polymer molecular weight (i.e. brush thickness), narrow polydispersities and control of the composition. In the two examples of generalized RAFT polymerization described above in Schemes 5 and 6, polymerization occurs prior to grafting to the gadolinium nanoparticle surfaces (i.e. "grafting to" the nanoparticle surface).

Functional Groups

Functional groups are groups that can be covalently linked to the polymer and/or covalently linked to the therapeutic or targeting agents, and/or bonded to the nanoparticles. The functional groups include any group that can be reacted with another compound to form a covalent linkage between the compound and the polymer extending from the nanoparticle. Exemplary functional groups can include carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives. The functional groups can be substituted or unsubstituted, as described herein.

Functional groups can be attached to the polymer during polymerization as depicted herein.

Alternatively, functional groups can be attached to the polymer backbone via a linker. The term "linker" as used herein refers to any chemical structure that can be placed between the polymer and functional group. For example, linkers include a group including alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxyalkyl groups. In various non-limited exemplary embodiments, the groups can be from $C_1$ to $C_{10}$, $C_{20}$, or $C_{30}$.

In various embodiments, the linker can include a conjugated bond, preferably selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —N═CH— and —N═CR—), —SiR═SiH—, and —SiR═SiR—), (—SiH═CH—, —CH═SiR—, and —CR═SiR—). Particularly certain bonds are acetylene, alkene, amide, and substituted derivatives of these three, and azo. The linker could also be carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). The linker could also be a peptidyl spacer such as Gly-Phe-Leu-Gly.

Therapeutic Agents and Targeting Agents

Figure 3:
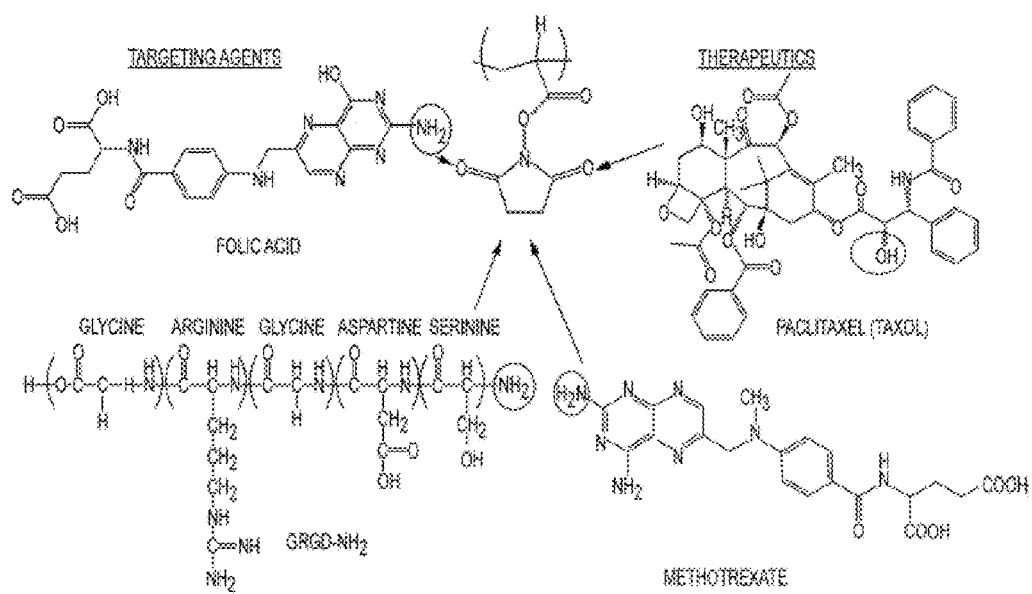
FIG. 3 depicts exemplary targeting molecules (folic acid or an RGD sequence) and exemplary therapeutic agents (the cancer therapeutics paclitaxel or methotrexate) binding to a functionalized polymer grafted to a nanoparticle.

Targeting agents and therapeutic agents can be covalently attached to the polymer. FIG. 3 shows an example of targeting molecules (folic acid or an RGD sequence) and an example therapeutic agents (the cancer therapeutics paclitaxel or methotrexate) binding to a functionalized polymer grafted to a nanoparticle. The functional groups attach to the polymer backbone by reaction with the succinimide functional group.

In various embodiments, the succinimide group of PNAOS provides an attachment point for a variety of targeting and therapeutic agents, such as, but not limited to, folic acid, GRGD sequences, Paclitaxel, and Methotrexate, through pre- and post-polymerization modification. Unreacted succinimide groups can further be converted to non-bioactive groups to reduce in vivo side reactions. Conjugation of therapeutic, targeting, and imaging agents to the copolymer provides a multifaceted system, which has potential in decreasing toxicity while increasing efficacy of the drug due to directed treatment through directed targeting with the ability to image through optical, magnetic resonance, or computer tomography.

It will be understood by those of skill in the art that various targeting agents or therapeutic agents can be selected for attachment to functional groups. Further, it will be understood that a linker can be placed between the functional groups and the targeting agents and therapeutic agents. The linker can be cleavable or non-cleavable. For example, in certain instances therapeutic agents can be cleavable. In certain instances, diagnostic agents can be non-cleavable.

Gold nanoparticles themselves can be therapeutic agents. Alteration of the shape and size of gold nanoparticles has proven a useful tool to kill cancer cells through near-infrared lasers and modification with poly(ethylene glycol) polymers has increased their biocompatibility. T. Niidome, et al., *J. Controlled Release*, 2006, 114, 343-347.

Targeting agents are compounds with a specific affinity for a target compound, such as a cell surface epitope associated with a specific disease state. Targeting agents may be attached to a nanoparticle surface to allow targeting of the nanoparticle to a specific target. Non-limiting examples of targeting agents include an amino acid sequence including the RGD peptide, an NGR peptide, folate, Transferrin, GM-CSF, Galactosamine, peptide linkers including growth factor receptors (e.g. IGF-1R, MET, EGFR), antibodies and antibody fragments including anti-VEGFR, Anti-ERBB2, Anti-tenascin, Anti-CEA, Anti-MUC1, Anti-TAG72, mutagenic bacterial strains, and fatty acids.

In various embodiments, targeting agents can be chosen for the different ways in which they interact with tumors. For example, when the targeting agent folic acid is taken into the cells by the folate receptors, RGD receptors are expressed on the surface of the cells, resulting in the nanostructures localizing to the cell surface. The folate receptor is known to be over expressed in cancer cells in the case of epithelial malignancies, such as ovarian, colorectal, and breast cancer, whereas in most normal tissue it is expressed in very low levels.

Targeting agents can include any number of compounds known in the art. In certain situations, the targeting agent specifically binds to a particular biological target. Nonlimiting examples of biological targets include tumor cells, bacteria, viruses, cell surface proteins, cell surface receptors, cell surface polysaccharides, extracellular matrix proteins, intracellular proteins and intracellular nucleic acids.

The nanoparticles and methods described herein are not limited to any particular targeting agent, and a variety of targeting agents can be used. The targeting agents can be, for example, various specific ligands, such as antibodies, monoclonal antibodies and their fragments, folate, mannose, galactose and other mono-, di-, and oligosaccharides, and RGD peptide. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to receptors. In some instances, a nanoparticle described herein can be conjugated to one, two, or more of a variety of targeting agents. For example, when two or more targeting agents are used, the targeting agents can be similar or dissimilar. Utilization of more than one targeting agent in a particular nanoparticle can allow the targeting of multiple biological targets or can increase the affinity for a particular target.

In some instances, the targeting agents are antigen binding proteins or antibodies or binding portions thereof. Antibodies can be generated to allow for the specific targeting of antigens or immunogens (e.g., tumor, tissue, or pathogen specific antigens) on various biological targets (e.g., pathogens, tumor cells, normal tissue). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')2); or biosynthetic antibodies, e.g., single chain antibodies, single domain antibodies (DAB), Fvs, or single chain Fvs (scFv).

Methods of making and using polyclonal and monoclonal antibodies are well known in the art, e.g., in Harlow et ah, Using Antibodies: A Laboratory Manual: Portable Protocol I. Cold Spring Harbor Laboratory (Dec. 1, 1998). Methods for making modified antibodies and antibody fragments (e.g., chimeric antibodies, reshaped antibodies, humanized antibodies, or fragments thereof, e.g., Fab', Fab, F(ab')2 fragments); or biosynthetic antibodies (e.g., single chain antibodies, single domain antibodies (DABs), Fv, single chain Fv (scFv), and the like), are known in the art and can be found, e.g., in Zola, Monoclonal Antibodies: Preparation and Use of Monoclonal Antibodies and Engineered Antibody Derivatives, Springer Verlag (Dec. 15, 2000; 1st edition). In some instances, the antibodies recognize tumor specific epitopes (e.g., TAG-72 (Kjeldsen et al, Cancer Res., 48:2214-2220 (1988); U.S. Pat. Nos. 5,892,020; 5,892,019; and 5,512,443); human carcinoma antigen (U.S. Pat. Nos. 5,693,763; 5,545,530; and 5,808,005); TPI and TP3 antigens from osteocarcinoma cells (U.S. Pat. No. 5,855,866); Thomsen-Friedenreich (TF) antigen from adenocarcinoma cells (U.S. Pat. No. 5,110,911); "KC-4 antigen" from human prostate adenocarcinoma (U.S. Pat. Nos. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA) (U.S. Pat. No. 4,914,021); a human pulmonary carcinoma antigen that reacts with human squamous cell lung carcinoma but not with human small cell lung carcinoma (U.S. Pat. No. 4,892, 935); T and Tn haptens in glycoproteins of human breast carcinoma (Springer et ah, Carbohydr. Res., 178:271-292 (1988)), MSA breast carcinoma glycoprotein (Tjandra et al, Br. J. Surg., 75:811-817 (1988)); MFGM breast carcinoma antigen (Ishida et al, Tumor Biol, 10: 12-22 (1989)); DU-PAN-2 pancreatic carcinoma antigen (Lan et al, Cancer Res., 45:305-310 (1985)); CA125 ovarian carcinoma antigen (Hanisch et ah, Carbohydr. Res., 178:29-47 (1988)); and YH206 lung carcinoma antigen (Hinoda et al, Cancer J., 42:653-658 (1988)). For example, to target breast cancer cells, the nanoparticles can be modified with folic acid, EGF, FGF, and antibodies (or antibody fragments) to the tumor-associated antigens MUC 1, cMet receptor and CD56 (NCAM).

Other antibodies that can be used recognize specific pathogens (e.g., *Legionella peomophilia, Mycobacterium tuberculosis, Clostridium tetani, Hemophilus influenzae, Neisseria gonorrhoeae, Treponema pallidum, Bacillus anthracis, Vibrio cholerae, Borrelia burgdorferi, Cornebacterium diphtheria, Staphylococcus aureus*, human papilloma virus, human immunodeficiency virus, rubella virus, and polio virus).

In some instances, the targeting agents include a signal peptide. These peptides can be chemically synthesized or cloned, expressed and purified using known techniques. Signal peptides can be used to target the nanoparticles described herein to a discreet region within a cell. In some situations, specific amino acid sequences are responsible for targeting the nanoparticles into cellular organelles and compartments. For example, the signal peptides can direct a nanoparticle described herein into mitochondria. In other examples, a nuclear localization signal is used.

In other instances, the targeting agent is a nucleic acid (e.g., RNA or DNA). In some examples, the nucleic acid targeting agents are designed to hybridize by base pairing to a particular nucleic acid (e.g., chromosomal DNA, mRNA, or ribosomal RNA). In other situations, the nucleic acids bind a ligand or biological target. For example, the nucleic acid can bind reverse transcriptase, Rev or Tat proteins of HIV (Tuerk et al, Gene, 137(I):33-9 (1993)); human nerve growth factor (Binkley et al, Nuc. Acids Res., 23(16):3198-205 (1995)); or vascular endothelial growth factor (Jellinek et al, Biochem., 83(34): 10450-6 (1994)). Nucleic acids that bind ligands can be identified by known methods, such as the SELEX procedure (see, e.g., U.S. Pat. Nos. 5,475,096; 5,270,163; and 5,475,096; and WO 97/38134; WO 98/33941; and WO 99/07724). The targeting agents can also be aptamers that bind to particular sequences.

The targeting agents can recognize a variety of epitopes on biological targets (e.g., pathogens, tumor cells, or normal cells). For example, in some instances, the targeting agent can be sialic acid to target HIV (Wies et al, Nature, 333:426 (1988)), influenza (White et al, Cell, 56:725 (1989)), Chlamydia (Infect. Immunol, 57:2378 (1989)), *Neisseria meningitidis, Streptococcus suis, Salmonella*, mumps, newcastle, reovirus, Sendai virus, and myxovirus; and 9-OAC sialic acid to target coronavirus, encephalomyelitis virus, and rotavirus; non-sialic acid glycoproteins to target cytomegalovirus (Virology, 176:337 (1990)) and measles virus (Virology, 172:386 (1989)); CD4 (Khatzman et al, Nature, 312:763 (1985)), vasoactive intestinal peptide (Sacerdote et al, J. of Neuroscience Research, 18: 102 (1987)), and peptide T (Ruff et al, FEBS Letters, 211: 17 (1987)) to target HIV; epidermal growth factor to target vaccinia (Epstein et al, Nature, 318: 663 (1985)); acetylcholine receptor to target rabies (Lentz et al, Science 215: 182 (1982)); Cd3 complement receptor to target Epstein-Barr virus (Carel et al, J. Biol. Chem., 265: 12293 (1990)); .beta.-adrenergic receptor to target reovirus (Co et al, Proc. Natl. Acad. ScL USA, 82: 1494 (1985)); ICAM-I (Marlin et al, Nature, 344:70 (1990)), N-CAM, and myelin-associated glycoprotein MAb (Shephey et al, Proc. Natl. Acad. ScL USA, 85:7743 (1988)) to target rhinovirus; polio virus receptor to target polio virus (Mendelsohn et al, Cell, 56:855 (1989)); fibroblast growth factor receptor to target herpes virus (Kaner et al, Science, 248: 1410 (1990)); oligomannose to target *Escherichia coli*; and ganglioside GMI to target *Neisseria meningitides*.

In other instances, the targeting agent targets nanoparticles according to the disclosure to factors expressed by oncogenes. These can include, but are not limited to, tyrosine kinases (membrane-associated and cytoplasmic forms), such as members of the Src family; serine/threonine kinases, such as Mos; growth factor and receptors, such as platelet derived growth factor (PDDG), SMALL GTPases (G proteins), including the ras family, cyclin-dependent protein kinases (cdk), members of the myc family members, including c-myc, N-myc, and L-myc, and bcl-2 family members.

In addition, vitamins (both fat soluble and non-fat soluble vitamins) can be used as targeting agents to target biological targets (e.g., cells) that have receptors for, or otherwise take up, vitamins. For example, fat soluble vitamins (such as vitamin D and its analogs, vitamin E, Vitamin A), and water soluble vitamins (such as Vitamin C) can be used as targeting agents.

In some embodiments, antibodies or ligands may be used to aid in site-specific targeting (T. M. Allen, *Nat. Rev. Cancer* 2, 750 (October, 2002), Y. S. Park, *Biosci. Rep.* 22, 267 (April, 2002)). Antibodies and antibody fragments are as described herein.

Therapeutic agents include any therapeutic compounds that are capable of preventing or treating a disease in a patient. Numerous therapeutic agents are known in the art. Non-limiting examples of therapeutic agents include doxorubicin, paclitaxel, methotrexate, cisplatin, camptothecin, vinblastine, aspartic acid analogues, and short interfering ribonucleic acid (siRNA) molecules.

In other embodiments, therapeutic agents can be, but are not limited to, steroids, analgesics, local anesthetics, antibiotic agents, chemotherapeutic agents, immunosuppressive agents, anti-inflammatory agents, antiproliferative agents, antimitotic agents, angiogenic agents, antipsychotic agents, central nervous system (CNS) agents; anticoagulants, fibrinolytic agents, growth factors, antibodies, ocular drugs, and metabolites, analogs, derivatives, fragments, and purified, isolated, recombinant and chemically synthesized versions of these species, and combinations thereof.

Representative useful therapeutic agents include, but are not limited to, tamoxifen, paclitaxel, anticancer drugs, camptothecin and its derivatives, e.g., topotecan and irinotecan, KRN 5500 (KRN), meso-tetraphenylporphine, dexamethasone, benzodiazepines, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, ellipticin, porphine derivatives for photo-dynamic therapy, and/or trioxsalen, as well as all mainstream antibiotics, including the penicillin group, fluoroquinolones, and first, second, third, and fourth generation cephalosporins. These agents are commercially available from, e.g., Merck & Co., Barr Laboratories, Avalon Pharma, and Sun Pharma, among others.

Additional classes of therapeutic agents include, but are not limited to, compounds for use in the following therapeutic areas: antihypertensives, antianxiety agents, antiarrythmia agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-angiogenesis agents, anti-glaucoma agents, anti-depressants, and antiviral agents.

Each named therapeutic agent should be understood to include the nonionized form of the therapeutic agent or pharmaceutically acceptable forms of the therapeutic agent. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrug agents.

Additional exemplary therapeutic agents suitable for use in the nanoparticles include, but are not limited to, phosphodiesterase inhibitors, such as sildenafil and sildenafil citrate; HMG-CoA reductase inhibitors, such as atorvastatin, lovastatin, simvastatin, pravastatin, fluvastatin, rosuvastatin, itavastatin, nisvastatin, visastatin, atavastatin, bervastatin, compactin, dihydrocompactin, dalvastatin, fluindostatin, pitivastatin, and velostatin (also referred to as synvinolin); vasodilator agents, such amiodarone; antipsychotics, such as ziprasidone; calcium channel blockers, such as nifedipine, nicardipine, verapamil, and amlodipine; cholesteryl ester transfer protein (CETP) inhibitors; cyclooxygenase-2 inhibitors; microsomal triglyceride transfer protein (MTP) inhibitors; vascular endothelial growth factor (VEGF) receptor inhibitors; carbonic anhydrase inhibitors; and glycogen phosphorylase inhibitors. Other low-solubility therapeutic agents suitable for use in the nanoparticles are disclosed in US Published patent application 2005/0031692, herein incorporated by reference.

Therapeutic compounds may also be used to achieve a desired prophylactic result, i.e. therapeutic compounds may be used prophylactively. Typically, prophylaxis is achieved prior to or at an earlier stage of disease than that treated by a therapeutic compound. Diagnostic compounds aid in determining whether a disease state exists in a patient. Alternatively, diagnostic compounds may aid in imaging, or measuring metabolic function.

In some embodiments, the compounds may be hydrophobic or partially hydrophobic (J. Lu, et al, *Small* 3, 1341 (August, 2007)). Hydrophobic compounds possess non-polar characteristics and thus not readily soluble in polar environments.

In other embodiments, the compounds may be or contain proteins or peptides (Slowing, I I, et al, *J. Am. Chem. Soc.* 129, 8845 (Jul. 18, 2007)). In further embodiments, the compounds may be DNA, RNA, or other nucleic acids (S. M. Solberg, C. C. Landry, *J. Phys. Chem. B* 110, 15261 (Aug. 10, 2006)). Compounds may also include biologics such as, without wishing to be limited by example, vaccines, blood products, and peptides. In some embodiments, more than one type of compound may be included in the porous framework core.

The nanoparticles described herein can be used to treat diseased cells and tissues. In this regard, various diseases are amenable to treatment using the nanoparticles and methods described herein. An exemplary, nonlimiting list of diseases that can be treated with the subject nanoparticles includes breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; non-Hodgkins lymphoma, multiple sclerosis, neuroblastoma and glioblastoma; T and B cell mediated autoimmune diseases; inflammatory diseases; infections; hyperproliferative diseases; AIDS; degenerative conditions, cardiovascular diseases, transplant rejection, and the like. In some cases, the treated cancer cells are metastatic.

The route and/or mode of administration of a nanoparticle described herein can vary depending upon the desired results. Dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner.

In some instances, a nanoparticle described herein is administered locally. This is achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, a nanoparticle described herein is introduced into the central nervous system, circulatory system or gastrointestinal tract by any suitable route, including intraventricular, intrathecal injection, paraspinal injection, epidural injection, enema, and by injection adjacent to the peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

A nanoparticle described herein is formulated as a pharmaceutical composition that includes a suitable amount of a physiologically acceptable excipient (see, e.g., Remington's Pharmaceutical Sciences pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Water is a particularly useful excipient when a nanoparticle described herein is administered intravenously. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in Remington's Pharmaceutical Sciences pp. 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. A nanoparticle described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, a nanoparticle described herein is formulated for intravenous administration. Compositions for intravenous administration can comprise a sterile isotonic aqueous buffer. The compositions can also include a solubilizing agent. Compositions for intravenous administration can optionally include a local anesthetic such as lignocaine to lessen pain at the site of the injection. The ingredients can be supplied either separately or mixed together in unit dosage form, for example, as a dry lyophilized powder or water-free concentrate in a hermetically sealed container such as an ampule or sachette indicating the quantity of active agent. Where a nanoparticle described herein is administered by infusion, it can be dispensed, for example, with an infusion bottle containing sterile pharmaceutical grade water or saline. Where a nanoparticle described herein is administered by injection, an ampule of sterile water for injection or saline can be provided so that the ingredients can be mixed prior to administration.

In other circumstances, a nanoparticle described herein can be administered across the surface of the body and the inner linings of the bodily passages, including epithelial and mucosal tissues. Such administrations can be carried out using a nanoparticle described herein in lotions, creams, foams, patches, suspensions, solutions, and suppositories (e.g., rectal or vaginal). In some instances, a transdermal patch can be used that contains a nanoparticle described herein and a carrier that is inert to the nanoparticle described herein, is non-toxic to the skin, and that allows delivery of the agent for systemic absorption into the blood stream via the skin. The carrier can take any number of forms such as creams or ointments, pastes, gels, or occlusive devices. The creams or ointments can be viscous liquid or semisolid emulsions of either the oil-in-water or water-in-oil type. Pastes of absorptive powders dispersed in petroleum or hydrophilic petroleum containing a nanoparticle described herein can also be used. A variety of occlusive devices can be used to release a nanoparticle described herein into the blood stream, such as a semi-permeable membrane covering a reservoir containing the nanoparticle described herein with or without a carrier, or a matrix containing the nanoparticle described herein.

Therapeutic agents and targeting agents can be covalently attached to the polymer by RAFT synthesis. The therapeutic agent or targeting agent is configured to be added to the RAFT polymer during polymerization. As such the therapeutic agent and targeting agent can be linked directly to the RAFT polymer. Those of skill in the art will recognize that a linker can be added between the therapeutic agent or targeting agent and the polymer.

Alternatively, therapeutic agents and targeting agents are linked to the polymer via a functional group as described above. Those of skill in the art will recognize that a linker can be added between the therapeutic agent or targeting agent and the polymer.

Multifunctional synthesis of compounds can be accomplished by RAFT polymerization as depicted in the example of Scheme 7.

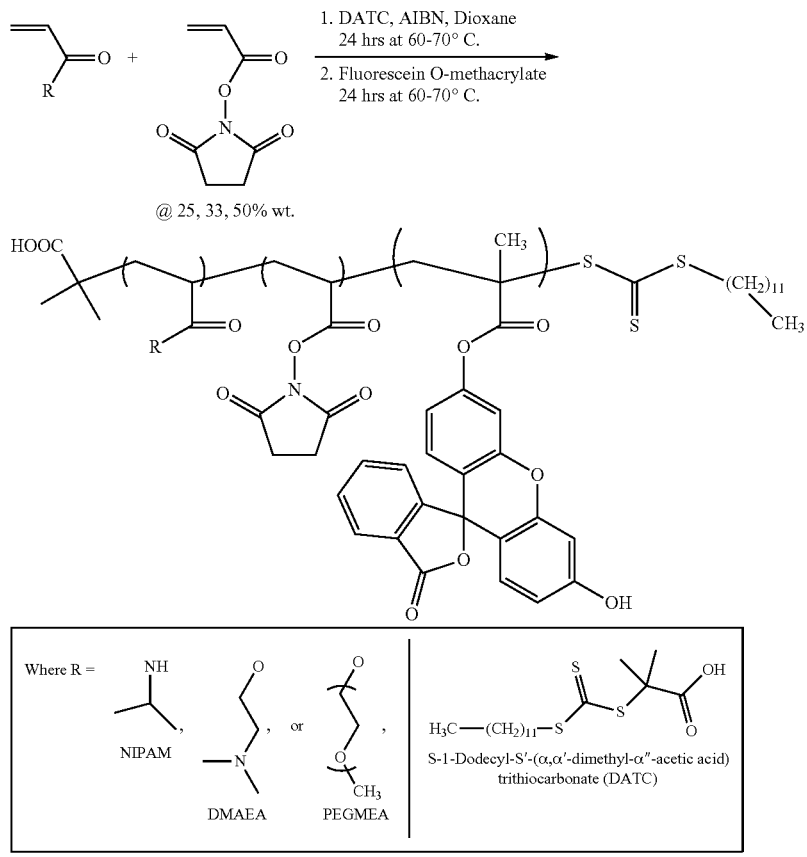

In this embodiment, a succinimide group can be used to attach a functional group to the nanoparticle. An example of biocompatible copolymers containing functional N-acryloyloxysuccinimide (NAOS) monomer units can also be synthesized via RAFT polymerization. A range of copolymer backbones can be used, including, but not limited to, N-isopropylacrylamide (NIPAM), N,N-dimethylaminoethyl acrylate (DMAEA), and poly(ethylene glycol) methyl ether acrylate (PEGMEA). The addition of NAOS into the copolymer backbones has been achieved at a range of weight percents as a means of attachment. The copolymers were synthesized utilizing the well-known trithiocarbonate DATC in dioxane at 60 or 70 degrees, with a fluorescein monomer incorporated near the end of the polymerization. The polymers were characterized via both proton NMR and GPC.

In various embodiments, unreacted succinimide groups can further be converted to non-bioactive groups to reduce in vivo side reactions.

In Scheme 8, a folic acid targeting agent is attached to the succinimide functional group.

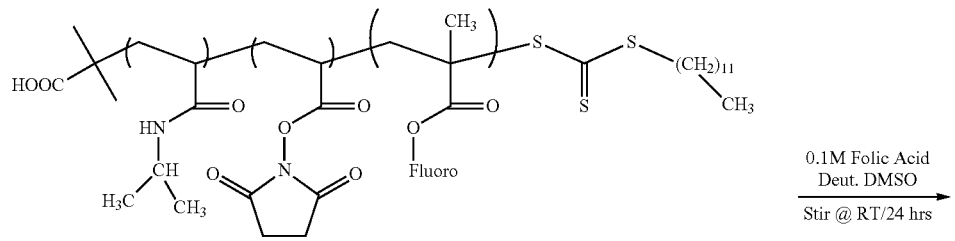

-continued

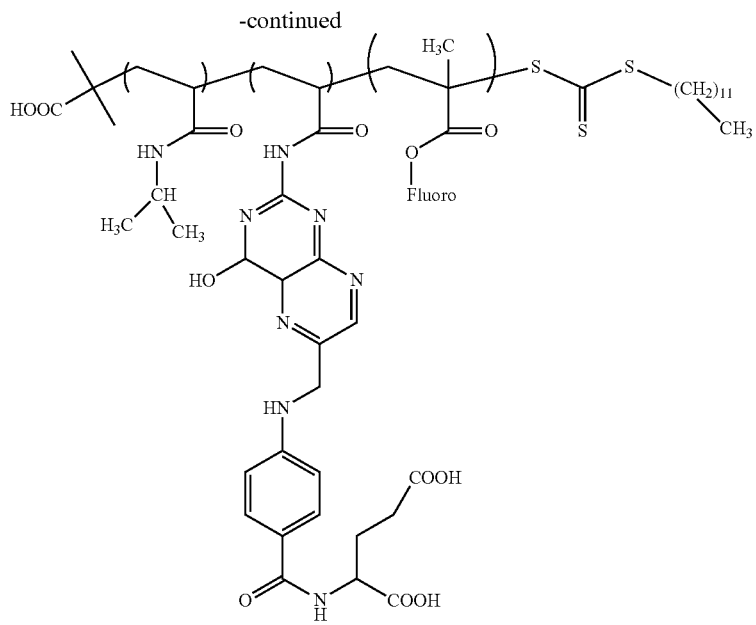

Figure 4:
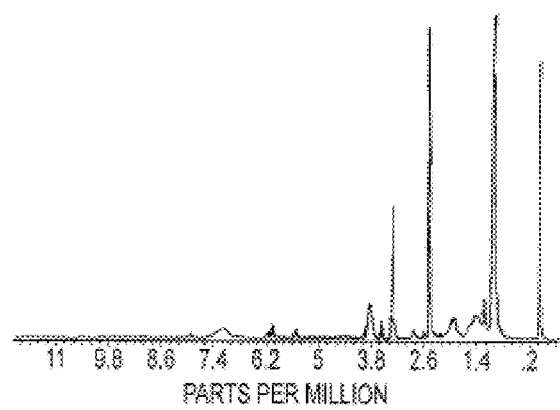
FIG. 4 depicts $^1$H NMR spectrum analysis of copolymer binding. (a) depicts a 1H NMR spectrum of PNIPAM-co-PNAOS-co-PFMA copolymer, (b) depicts a $^1$H NMR spectrum of folic acid, (c) depicts a $^1$H NMR spectrum of PNIPAM-co-PNAOS-co-PFMA copolymer reacted with folic acid.
Figure 4:
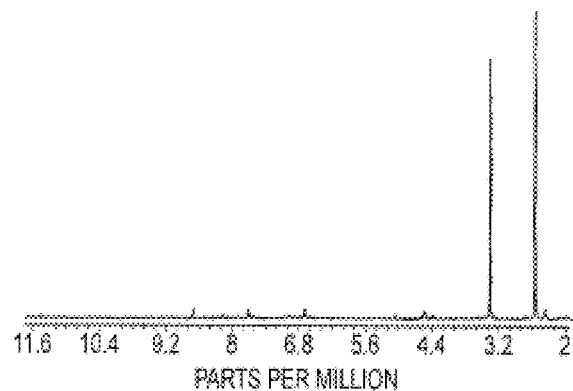
Figure 4:
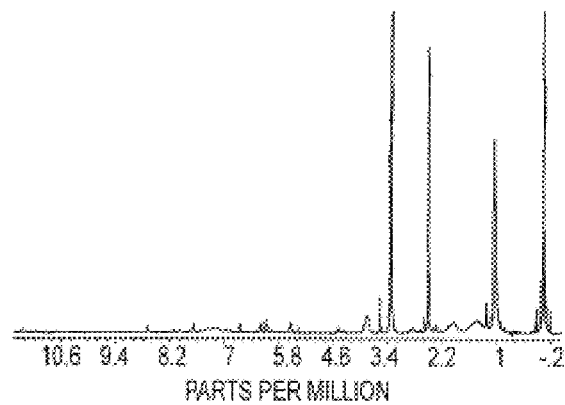

FIG. 4a depicts a ¹H NMR spectrum of PNIPAM-co-PNAOS-co-PFMA copolymer. FIG. 4b depicts a ¹H NMR spectra of folic acid. FIG. 4c depicts a ¹H NMR spectrum of PNIPAM copolymer reacted with folic acid.

Imaging Agents

A particularly interesting aspect of nanomedicines is multimodal imaging agents. Biomedical imaging and diagnostic techniques such as computed X-ray tomography (CT), magnetic resonance imaging (MRI), optical imaging (OI) and positron emission tomography (PET) are useful in modern clinical settings for the diagnosis of various diseases. While these imaging techniques have been responsible for tremendous advances in clinical diagnosis, each has its own advantages and drawbacks, and no single technique includes all the required capabilities for comprehensive biomedical imaging.

Imaging agents can be covalently attached to the polymer. The imaging agents may be attached to a functionalized group on the polymer backbone grafted to a nanoparticle. The functional groups attach to the polymer backbone by reaction with the succinimide functional group. Those of skill in the art will recognize that many different imaging agents that can be attached to the polymer backbone. Without being limited to specific embodiments, imaging agents can be chosen from the group comprising fluorescence agents, radiological agents, and positron emission agents.

Current magnetic resonance imaging (MRI) techniques employ gadolinium as a contrast agent. In certain embodiments, gadolinium metal is highly toxic to cells. For MRI application, this toxicity has been overcome by utilizing chelates to increase stability and compatibility of the metal ion. However, concerns have arisen with current in vivo use of gadolinium chelates due to non-specific cellular uptake and accumulation within healthy cells. W. A. High, *J. Am. Acad. Dermatol.* 2006, 56, 21-26. Several groups have attempted to overcome these issues by using cascade polymers and dendrimers, however size distribution and spatial loading is poor. Id. Gadolinium oxide nanoparticles have proven to be interesting because of their effectiveness as MRI contrast agents. J. L. Bridot, *J. Am. Chem. Soc.* 2007. H. Hifumi, *J. Am. Chem. Soc.* 2006, 128, 15090-15091, W. J. Rieter, *J. Am. Chem. Soc.* 2006, 128, 9024-9025. M. O. Oyewumi, *Journal of Controlled Release* 2004, 95, 613-626. Modification of these particles with polymers shows promise as a means to compatiblize the surface of gadolinium nanoparticles for in vivo imaging and to affix moieties that will potentially allow for targeting and treatment of cancer cells through control of nanoparticle-cellular surface interactions. Though recent advances have been made in the synthesis and modification of metal nanoparticles, such as gold nanorods, the modification and characterization of metal oxide frameworks, such as gadolinium oxide nanoparticles, is still limited.

Fluorescence agents can be visualized in the visible or near-visible spectra. Fluorescence agents [such as PFMA are induced to emit photons by exciting electrons in the molecules by exposure to light energy, typically violet or ultraviolet light.]. Radiological agents are molecules possessing radioactive material that can be detected by detection of the radioactive decay. Positron emission tomography (PET) agents contain radioactive materials that can be detected by a gamma or PET scanner.

It will be understood by those of skill in the art that various imaging agents can be selected for attachment to functional groups. Further, it will be understood that a linker can be placed between the functional groups and the imaging agents. The linker can be cleavable or non-cleavable. For example, in certain instances imaging agents can be cleavable. In certain instances, imaging agents can be non-cleavable.

Without wishing to be limited by specific embodiments, Gold/Lanthanide nanoparticles can be modified with a well-defined RAFT copolymer, PNIPAM-co-poly(N-acryloxy-succinmide)(PNAOS)-co-poly(fluorescein O-methacrylate) (PFMA). Incorporation of the PFMA monomer into the backbone of the copolymer provides a means measuring polymer incorporation in vitro by fluorescence imaging. In order to confirm the ability of these copolymer modified hybrid nanoparticles to be imaged by fluorescence microscopy, a fluorescence scanner was employed to provide the images of PNIPAM-co-PNAOS-co-PFMA modified gold/

Figure 5:
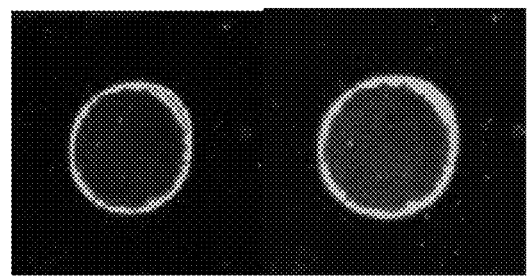
FIG. 5 depicts fluorescence images of PNIPAM-co-PNAOS-co-PFMA modified gold/Gd nanoparticles.

Gd nanoparticles (FIG. 5). Fluorescence of these particles is readily detectible in copolymer modified gold/lanthanide nanoparticles.

Multimodal Imaging

In some aspects different imaging agents may be combined to produce a multimodal imaging agent. By way of example and not limitation, multimodal imaging agents may combine PET and CT, PET and MRI, or MRI and OI. (Bakalova et al, Multimodal Silica Shelled Quantum Dots: Direct Intracellular Delivery, Photosensitization, Toxic, and Microcirculation Effects. Bioconjugate Chem. 19, 1135-1142 (2008); Frullano, L., Meade, T. J. Multimodal MRI Contrast Agents. *J. Biol. Inorg. Chem.* 12, 939-949 (2007)) In some aspects, these imaging techniques may be complimentary, rather than competitive, and so may aid in minimizing artifacts and enabling precise comparative analysis of images obtained by the different techniques. (Frullano, L., Meade, T. J. Multimodal MRI Contrast Agents. *J. Biol. Inorg. Chem.* 12, 939-949 (2007)).

Gadolinium Based Imaging

MRI, magnetic resonance imaging, involves measuring the nuclear magnetic resonance (NMR) of water protons in a specimen. This may be performed by placing a subject in a magnetic field that may re-orient protons and measuring the time for the affected protons to relax. Protons in differing chemical environments will exhibit different relaxation times. The observed contrast in MRI essentially depends on factors such as the water proton density, the longitudinal relaxation time (T1), and the transverse relaxation time (T2) of these protons. Contrast agents may be used in MRI to aid in diagnostic imaging.

Gadolinium may be used to enhance MRI. (Aime et al, $R_2/R_1$ Ratiometric Procedure for a Concentration-Independent, pH-Responsive, Gd(III)-Based MRI Agent. *J. Am. Chem. Soc.* 128, 11326-11327 (2006); Bridot et al., Hybrid Gadolinium Oxide Nanoparticles: Multimodal Contrast Agents for in Vivo Imaging. *J. Am. Chem. Soc.* 129, 5076-5084 (2007); Hifumi et al., Gadolinium-Based Hybrid Nanoparticles as a Positive MR Contrast Agent. *J. Am. Chem. Soc.* 128, 15090-15091 (2006)). MRI agents may work by increasing the contrast (or relaxation rate of protons) between the particular organ or tissue of interest and the surrounding tissues in the body. (Caravan, P., Ellison, J. J., McMurry, T. J., Lauffer, R. B. Gadolinium(III) Chelates as MRI Contrast Agents: Structure, Dynamics, and Application. *Chem. Rev.* 99, 2293-2352 (1999).) These agents may have a local effect on T1 and T2 relaxation times. In one aspect, relaxivity of water protons may be altered by introducing a high spin paramagnetic metal into the system. For example, gadolinium (Gd), may be used to alter proton relaxation times. In some aspects, water molecules bound to Gd may relax orders of magnitude faster than free water, resulting in dramatic changes in T1 where Gd is present. Gadolinium(III) ($Gd^{3+}$) complexes may have a high longitudinal relaxivity ($r_1$) and thus have an effect mostly on T1-relaxation times of surrounding water protons (as described in Caravan et al., Gadolinium(III) Chelates as MRI Contrast Agents: Structure, Dynamics, and Application. *Chem. Rev.* 99, 2293-2352 (1999)). This enhanced T1-relaxation time may lead to an increase in signal intensity in T1-weighted images.

Gold Based Imaging

Gold (Au), because of its high atomic number and X-ray absorption coefficient may be used to in various imaging techniques known in the art. (Kim, D., Park, S., Lee, J. H., Jeong, Y. Y., Jon, S. Antibiofouling Polymer-Coated Gold Nanoparticles as a Contrast Agent for in Vivo X-ray Computed Tomography Imaging. *J. Am. Chem. Soc.* 129, 7661-7665 (2007); Su, C.-H., Sheu, H.-S., Lin, C.-Y., Huang, C.-C., Lo, Y.-W., Pu, Y.-C., Weng, J.-C., Shieh, D.-B., Chen, J.-H., Yeh, C.-S. Nanoshell Magnetic Resonance Imaging Contrast Agents. *J. Am. Chem. Soc.* 129, 2139-2146 (2007); Huang, X., EI-Sayed, I. H., Qian, W., EI-Sayed, M. A. Cancer Cell Imaging and Photothermal Therapy in the Near-Infrared Region by Using Gold Nanorods. *J. Am. Chem. Soc.* 128, 2115-2120 (2006)). By way of example and not limitation, gold nanoparticles may be used to enhance images produced by X-ray computed tomography (CT; as described in Kim et al, Antibiofouling Polymer-Coated Gold Nanoparticles as a Contrast Agent for in Vivo X-ray Computed Tomography Imaging. *J. Am. Chem. Soc.* 129, 7661-7665 (2007)), and dark field and confocal microscopy (as described in Huang, X., EI-Sayed, I. H., Qian, W., EI-Sayed, M. A. Cancer Cell Imaging and Photothermal Therapy in the Near-Infrared Region by Using Gold Nanorods. *J. Am. Chem. Soc.* 128, 2115-2120 (2006)). Dark field and confocal microscopy are optical imaging techniques that may aid visualization by increasing contrast. CT is a non-optical imaging technique that may involve constructing a three dimensional representation of a specimen from a series of two dimensional X-ray images.

Other Methods

Aside from the in vivo diagnosis and treatment of cancer, with attachment of appropriate therapeutics and/or targeting moieties and/or imaging agents, the invention may be used for a wide variety of different drug delivery applications, such as gene therapy, imaging applications, such as vascular imaging, and even in external molecular detection devices, such as microarrays and assays. The primary industry interested in the invention would be pharmaceutical companies. While these applications have been mentioned specifically there may be many more applications that the inventors have not considered or are yet to be thought of for the invention.

EXAMPLES

The following examples are intended to be exemplary, and not limit, the present disclosure.

Example 1 Synthesis of Gold/Gadolinium Nanoparticles

Figure 6:
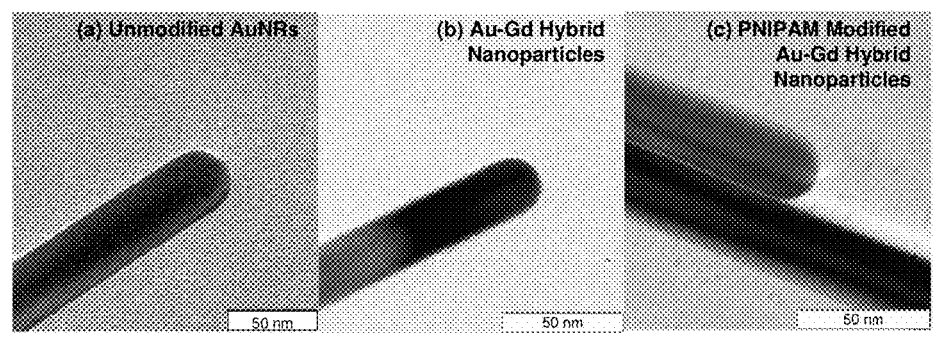
FIG. 6 depicts transmission electron microscopy (TEM) images of (a) unmodified gold nanoparticles (Au NPs), (b) gold/gadolinium (Au/Gd) nanoparticles, and (c) PNIPAM homopolymer modified gold/Gd nanoparticles

Gold nanoparticles were synthesized via procedures described herein. As shown in FIG. 6(a), one embodiment resulted in synthesized gold nanoparticles having an average length of 250 nm and width of 30 nm, providing an aspect ratio (length/width) of about 8 nm. Those of skill in the art will appreciate that the average dimensions of gold nanoparticles can be easily tuned with slight changes to the experimental procedures.

Gold nanoparticles were subsequently coated with a Gd-based nanoscale metal organic framework (NMOF). Coating of the gold nanoparticles was accomplished by taking advantage of a reverse microemulsion system, discussed in the literature and depicted in FIG. 1. In one embodiment reverse microemulsion provides Gd-based NMOFs. For Gd-based NMOFs, aqueous solutions of $GdCl_3$ (0.5M) and 1,4-benzenedicarboxylic acid (1,4-BDC) (0.075M) were first prepared separately. Next, the $GdCl_3$ and 1,4-BDC aqueous solutions were combined into a heptane/hexanol/cetyltrimethylammonium bromide (0.05M) microemulsion. This was followed by addition of the gold nanoparticles into the microemulsion reaction. The nanoparticle/gadolinium mixture was then stirred vigorously for 24 hours at room temperature.

After 24 h, the microemulsion mixture was centrifuged; the supernatant removed, and the nanoparticles subjected to three cycles of ethanol-wash/sonication/centrifugation. The supernatant was collected and discarded. The gold/gadolinium nanoparticles were then subjected to one last wash in deionized water followed by centrifugation and then storage in fresh deionized water. The gold/Gd nanoparticles were characterized by TEM (transmission electron microscopy), UV-Vis (ultraviolet visual) spectroscopy, and ATR-FTIR (attenuated total reflection-fourier transform infrared).

Transmission Electron Microscopy, TEM, was used to visualize and measure the Gd-coated gold nanoparticles. TEM identified a uniform Gd-based coating of the gold nanoparticles with an average thickness of 4 nm (FIG. 6b).

Figure 7:
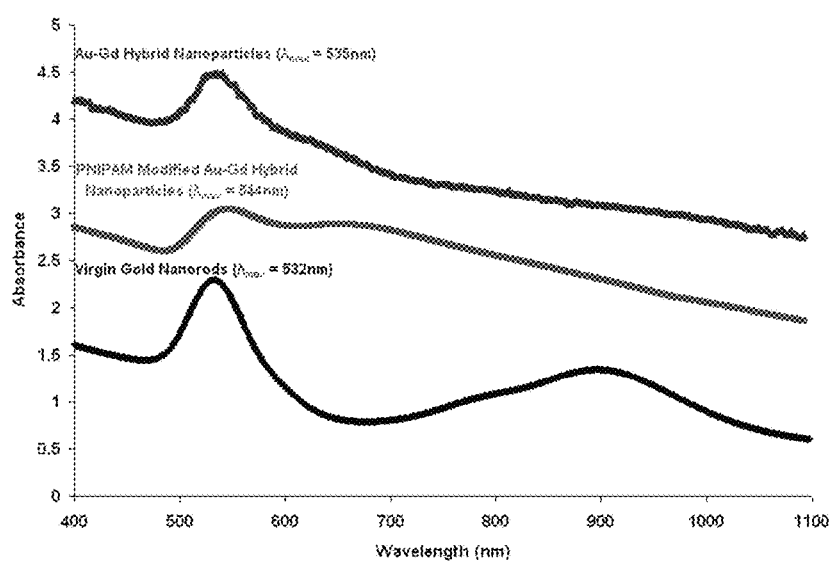
FIG. 7 depicts UV-Vis spectra of virgin gold nanoparticles, gold-gadolinium (Au—Gd) hybrid nanoparticles, and poly(N-isopropylacrylamide) modified Au—Gd hybrid nanoparticles

Ultraviolet-Violet spectroscopy was also used to analyze the Gd-coated gold nanoparticles. This technique was first used to analyze the virgin gold nanoparticles (FIG. 7), which gave a wavelength maximum for the transverse surface plasmon peak of 532 nm. Coating these particles with Gd-based metal organic framework resulted in a red shift of the transverse surface plasmon peak maximum to 535 nm (FIG. 7). This 3 nm red shift correlated well to the thickness of the surface coating measured by TEM (FIG. 6b).

Figure 8:
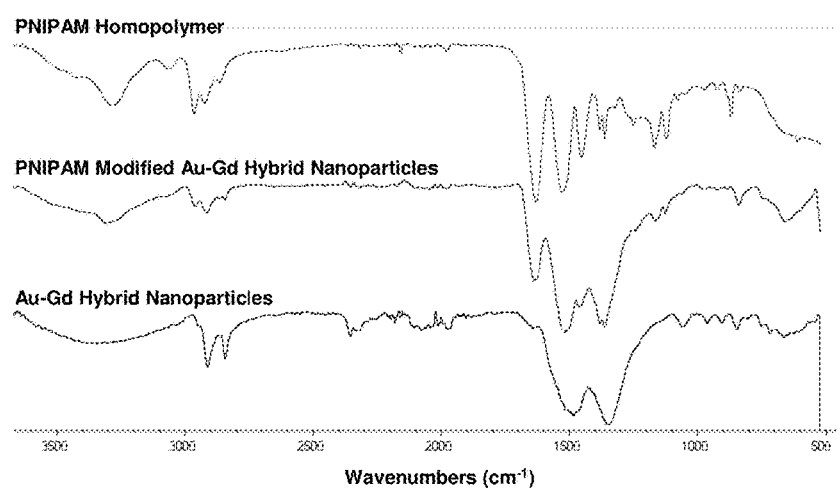
FIG. 8 depicts ATR-FTIR (attenuated total reflection-fourier transform infrared) spectra of gold-gadolinium (Au/Gd) nanoparticles, poly(N-isopropylacrylamide) (PNIPAM) homopolymer synthesized via RAFT polymerization, and PNIPAM modified Au—Gd hybrid nanoparticles.

Finally, ATR-FTIR was also used to analyze the gadolinium coated nanoparticles. ATR-FTIR was used to probe the structure of the gadolinium-coated gold nanoparticles (FIG. 8). The gadolinium-coated gold nanoparticles produced a spectrum with a characteristic out-of-plane=C—H aromatic stretch at 725 cm$^{-1}$, symmetric carboxylate stretch at 1450 cm$^{-1}$, an assymetric carboxylate stretch at 1520 cm$^{-1}$, along with 2855 cm$^{-1}$, 2925 cm$^{-1}$, and 3065 cm$^{-1}$. These peaks are attributed to the —C—H stretching vibrations of the 1,4-BDC bridging ligand. There was also a 3460 cm$^{-1}$ peak which was attributed to the —OH stretch of the water ligand.

Thus these techniques confirmed the presence of a gadolinium coating on the gold nanoparticles that was measured to be approximately 3 to 4 nm thick.

Example 2 Polymer Surface Modification of Au—Gd Hybrid Nanoparticles

Scheme 1.

Au/Gd hybrid nanoparticles were modified with well-defined homopolymers and copolymers synthesized via reversible addition-fragmentation chain transfer (RAFT) polymerization. Without being limited to a specific mechanism or mode of action, one mechanism of attachment is shown in FIG. 1d. In the mechanism depicted in FIG. 1d, a thiolate terminated polymer is covalently attached to the nanoparticle surface through a coordination reaction between the polymer chain thiolate end-group moiety and vacant orbitals on the Gd$^{3+}$ ions at the surface of the Gd nanoparticles.

In one embodiment, DATC was employed as the RAFT agent in the formation of homopolymers by RAFT polymerization. This DATC/RAFT reaction yields trithiocarbonate terminated chains. Au/Gd hybrid nanoparticles were modified with poly(N-isopropylacrylamide) (PNIPAM) homopolymer in N,N-dimethylformamide with the use of hexylamine as a reducing agent (Scheme 2). Modification of Au/Gd nanoparticles was achieved by an initial aminolysis, using hexylamine, of the trithiocarbonate end group of the RAFT homopolymer to a thiolate functionality under inert and basic conditions. Subsequently, the thiolate terminated homopolymer was covalently attached to the nanoparticle surface through a coordination reaction between the polymer and Gd3+.

After polymer deposition and prior to characterization or use, the nanoparticles were washed several times with a good solvent in order to remove any free polymer from the system.

The polymer modification of the Au/Gd nanoparticles with the PNIPAM homopolymer was analyzed by TEM (FIG. 6), UV-Vis spectroscopy (FIG. 7), and ATR-FTIR (FIG. 8). All three methods confirmed the presence of polymer modification on the nanoparticle.

TEM was again used to measure the thickness of the gold/gadolinium/polymer surface. This technique resulted in a measurement for the thickness of the gadolinium/polymer layer of approximately 8 nm. Subtracting out the apparent thickness of the gold/gadolinium layer (4 nm) suggested that the polymer layer was 4 nm thick. These values agreed well with results obtained by surface plasmon shift/UV-Vis spectroscopy.

FIG. 7 shows that the maximum surface plasmon peak of the gold/gadolinium/polymer nanoparticles occurred at 544 nm. Comparing the UV/Vis spectra of gold nanoparticles, gold/gadolinium nanoparticles, and gold/gadolinium/polymer nanoparticles showed a 12 nm shift in surface plasmon peak between the gold nanoparticle and the gold/gadolinium/polymer nanoparticles. This represents a 9 nm red shift from gold/gadolinium nanoparticle to gold/gadolinium/polymer nanoparticle.

Finally, ATR-FTIR analysis identified significant N—H bonding and other changes in the spectrum of Au/Gd polymer nanoparticles compared to unmodified Au/Gd nanoparticles or homopolymer (FIG. 8). Several of the characteristic stretches of the free PNIPAM homopolymer, including a broad N—H stretch above 3300 cm$^{-1}$ and a small N—H bend at 1640 cm$^{-1}$ indicating the presence of the acrylamide functionality; an increase in intensity of the —CH2 stretching and C—H stretching vibrations between 2800-3000 cm$^{-1}$ due to backbone methylenes; a peak at 1720 cm$^{-1}$ assigned to the carbonyl stretch of the amide; and a stretch at 1380 cm$^{-1}$ attributed to the addition of —CH3 and isopropyl groups, display good transference to the polymer modified Au/Gd hybrid nanoparticles, when compared to the unmodified Au/Gd hybrid nanoparticles (FIG. 8).

Scheme 2.

Surface Modification of Au/Gd Hybrid Nanoparticles by Incorporation of Optical Imaging Agents into Polymer Backbone. Fluorescence imaging was used to analyze polymer modification of Au/Gd nanoparticles. Incorporation of a poly(fluorescein O-methacrylate) monomer into the backbone of the copolymer would provide a means for measuring polymer incorporation through the use of in vitro fluorescence imaging. To do this, Au/Gd hybrid nanoparticles were first modified with a fluorescent RAFT copolymer, PNIPAM-co-poly(N-acryloxysuccinimide)(PNAOS)-co-poly (fluorescein O-methacrylate) (PFMA).

A fluorescence scanner was used in order to confirm incorporation and provide images of fluorescent gold/Gd nanoparticles. FIG. 5 is a flourescence image of gold/gadolinium nanoparticles coated with a fluoescent copolymer.

Example 3 Biocompatibilty of Gold/Gadolinium Nanoparticles

The ability of modified and unmodified Au/Gd nanoparticles to inhibit cell growth was compared in vitro.

Figure 9:
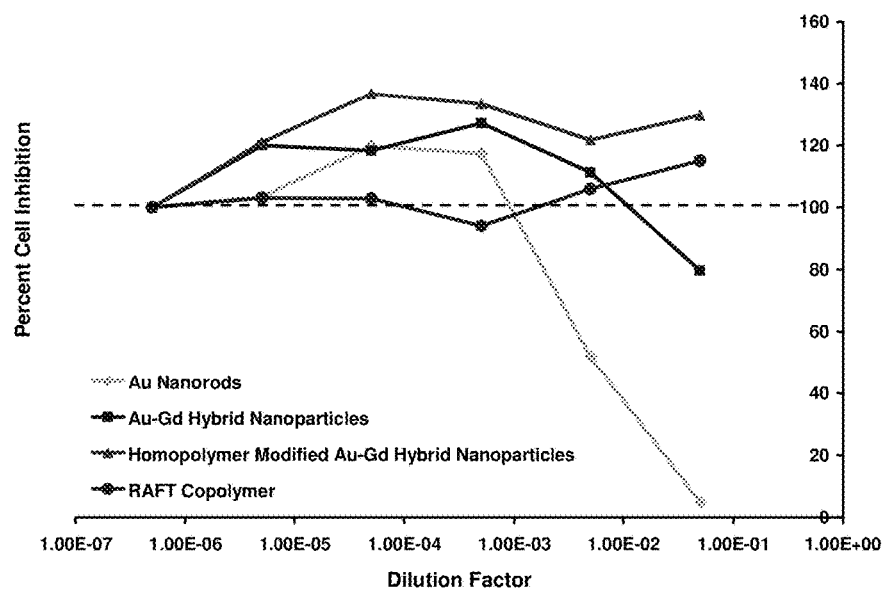
FIG. 9 depicts cell inhibition studies for unmodified gold nanoparticles and Au—Gd hybrid nanoparticles, homopolymer modified gold/Gd nanoparticles, and the reversible addition-fragmentation chain transfer (RAFT) copolymer, PNIPAM-co-PNAOS-co-PFMA.

To test the biocompatibility of the unmodified and polymer modified gold/Gd nanoparticles, growth inhibition studies were performed using a canine endothelial hemangiosarcoma (FITZ-HSA) tumor cells. Samples were incubated with FITZ-HSA at 37° C. in standard culture medium containing 10% PBS for 72 h in a 5% CO2 atmosphere. Each of the components for the nanodevice synthesis, gold nanoparticles, RAFT copolymer, along with the unmodified and polymer-modified gold/Gd nanoparticles were tested. As can be seen in FIG. 9, the unmodified gold nanoparticles resulted in significant cell growth inhibition at high concentrations. This is most likely due to residual CTAB absorbed on the surface of the gold nanoparticles. However, note that modification of the gold nanoparticles to form the gold/Gd nanoparticles and further modification of the gold/Gd nanoparticles did not decrease cell viability. The increased cell viability is attributed to coating of the gold/Gd nanoparticles with copolymers consisting of the biocompatible polymer PNIPAM. This infers that the presence of the RAFT copolymer on the surface of the gold/Gd nnaoparticles increases the biocompatible nature of the nanodevice.

In vitro MRI of GdNPs and Polymer Modified Gd NPs. In order to provide information about the clinical imaging viability of the polymer modified gold/Gd nanoparticles, as a positive contrast agent, in vitro MRI was employed to determine relaxation properties of the unmodified and polymer modified gold/Gd nanoparticles. Table 1 compares the MRI longitudinal and transverse relaxivities, r1 and r2, respectively, of PNIPAM-modified gold/Gd nanoparticles and gold/Gd unmodified nanoparticles to the clinically employed contrasts agents, gadopentetate dimeglumine (Magnevist®) and gadobenate dimeglumine (Multihance®). The calculated relaxivities demonstrate that both the unmodified and polymer modified Gd NPs result in a large shortening of the T1 relaxation time and, thus, behave as positive contrast agents. Additionally, the ratio of the transverse and longitudinal relaxivities of the unmodified and polymer modified gold/Gd nanoparticles are less than that of the clinically employed contrast agents, Magnevist® and Multihance®, suggesting that unmodified and polymer-modified Gd NPs should produce potentially feasible clinically useful T1 shortening effects, in comparison to currently employed contrast agents. By taking advantage of these properties, novel theragnostic polymer-modified gold/Gd nanoparticles could be produced and exploited as contrast agents for conventional T1 MR imaging.

TABLE 1

MRI relaxivity values for clinical MRI contrast agents, Multihance ® and Magnevist ®, along with the unmodified and polymer modified gold/Gd nanoparticles.

| Contrast Agent | $r_1$ (mM/L) | $r_2$ (mM/L) | $r_2/r_1$ |
|---|---|---|---|
| Magnevist ® | 6.95 | 17.41 | 2.51 |
| Multihance ® | 17.70 | 35.57 | 2.01 |
| Unmodified Au—Gd Hybrid NPs | 6.08 | 8.22 | 1.35 |
| PNIPAM Homopolymer Modified Au—Gd Hybrid NPs | 11.28 | 18.83 | 1.67 |
| PNIPAM Copolymer Modified Au—Gd Hybrid NPs | 13.55 | 21.85 | 1.61 |

Applicants further note that the compounds and methods disclosed herein include those compounds cited in U.S. 2007/0123670 to McCormick et al., which is incorporated herein by reference in its entirety.

All references cited herein are incorporated herein by reference in their entirety.

We claim:

1. A method of making a nanoparticle conjugate comprising:
   contacting a compound of Formula (III) or salt thereof with a compound of Formula (V) or a salt thereof to form a compound of Formula (VI):

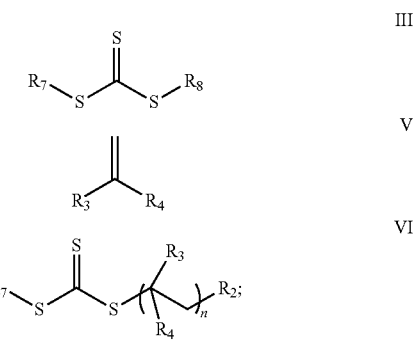

contacting the compound of Formula (VI) with a gold nanoparticle having a lanthanide-containing metal organic framework disposed thereon to form a nanoparticle conjugate having the compound of Formula (VI) grafted directly onto the lanthanide-containing metal organic framework;
wherein n is an integer, and
$R_2$, $R_3$, $R_4$, $R_7$, and $R_8$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

2. A method of making a nanoparticle conjugate comprising:
   contacting a compound of Formula (II) or salt thereof with a compound of Formula (V) or a salt thereof to form the compound of Formula (VI):

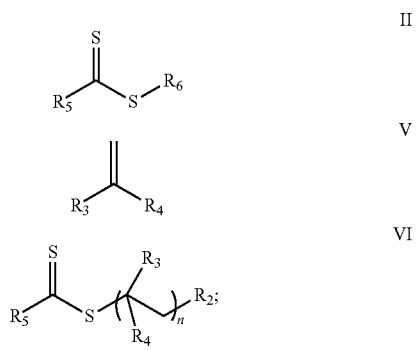

contacting the compound of Formula (VI) with a gold nanoparticle having a lanthanide-containing metal organic framework disposed thereon to form a nanoparticle conjugate;

wherein n is an integer, and $R_2$, $R_3$, $R_4$, $R_5$, and $R_8$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

3. The method of claim 1, further comprising:
contacting the compound of Formula VI with a reducing agent in the presence of the nanoparticle.

4. The method of claim 2, further comprising:
contacting the compound of Formula VI with a reducing agent in the presence of the nanoparticle.

5. The method of claim 3, wherein the reducing agent is hexylamine.

6. The method of claim 1, comprising disposing the metal organic framework on the gold nanoparticle by a reverse microemulsion reaction.

7. The method of claim 6, wherein the microemulsion reaction comprises combining aqueous solutions of each of GdCl3 and 1,4-benzenedicarboxylic acid into a heptane/hexanol/cetyltrimethylammonium bromide microemulsion.

8. The method of claim 1, comprising forming initiators on the metal organic framework surface, wherein the initiators are configured to facilitate polymer formation or polymer precursor binding.

9. The method of claim 1, wherein the step of contacting is a step in reversible addition-fragmentation chain transfer (RAFT) polymerization.

10. The method of claim 1, wherein the compound of Formula (VI) is covalently grafted directly onto the lanthanide-containing metal organic framework.

11. The method of claim 1, further comprising polymerization of the compound of Formula (VI) prior to contacting the compound of Formula (VI) with the gold nanoparticle having the lanthanide-containing metal organic framework disposed thereon.

12. The method of claim 1, wherein the nanoparticle conjugate has the chemical structure of Formula (I):

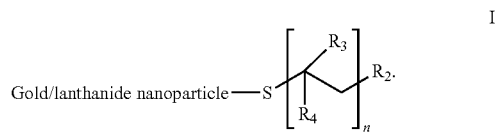

13. The method of claim 4, wherein the reducing agent is hexylamine.

14. The method of claim 2, comprising disposing the metal organic framework on the gold nanoparticle by a reverse microemulsion reaction.

15. The method of claim 14, wherein the microemulsion reaction comprises combining aqueous solutions of each of $GdCl_3$ and 1,4-benzenedicarboxylic acid into a heptane/hexanol/cetyltrimethylammonium bromide microemulsion.

16. The method of claim 2, comprising forming initiators on the metal organic framework surface, wherein the initiators are configured to facilitate polymer formation or polymer precursor binding.

17. The method of claim 2, wherein the step of contacting is a step in reversible addition-fragmentation chain transfer (RAFT) polymerization.

18. The method of claim 2, wherein the compound of Formula (VI) is covalently grafted to the gold nanoparticle having the lanthanide-containing metal organic framework disposed thereon.

19. The method of claim 2, further comprising polymerization of the compound of Formula (VI) prior to contacting the compound of Formula (VI) with the gold nanoparticle having the lanthanide-containing metal organic framework disposed thereon.

20. The method of claim 2, wherein the nanoparticle conjugate has the chemical structure of Formula (I):

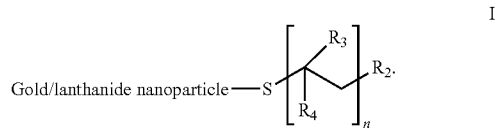

* * * * *

UNITED STATES PATENT AND TRADEMARK OFFICE
CERTIFICATE OF CORRECTION

PATENT NO. : 10,406,111 B2  
APPLICATION NO. : 14/637130  
DATED : September 10, 2019  
INVENTOR(S) : Stephen G. Boyes et al.

Page 1 of 1

It is certified that error appears in the above-identified patent and that said Letters Patent is hereby corrected as shown below:

In the Claims

Column 45, Line 36, Claim 7, Line 3:
"GdCl3"
Should read:
--$GdCl_3$--

Signed and Sealed this  
Thirty-first Day of December, 2019

Andrei Iancu  
*Director of the United States Patent and Trademark Office*